(12) United States Patent
Lachia et al.

(10) Patent No.: US 9,598,363 B2
(45) Date of Patent: Mar. 21, 2017

(54) PLANT GROWTH REGULATING COMPOUNDS

(71) Applicant: SYNGENTA PARTICIPATIONS AG, Basel (CH)

(72) Inventors: Mathilde Denise Lachia, Stein (CH); Alain De Mesmaeker, Stein (CH); Claudio Screpanti, Stein (CH); Hanno Christian Wolf, Stein (CH); Pierre Joseph Marcel Jung, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/770,202

(22) PCT Filed: Feb. 27, 2014

(86) PCT No.: PCT/EP2014/053854
§ 371 (c)(1),
(2) Date: Aug. 25, 2015

(87) PCT Pub. No.: WO2014/131843
PCT Pub. Date: Sep. 4, 2014

(65) Prior Publication Data
US 2016/0002161 A1   Jan. 7, 2016

(30) Foreign Application Priority Data

Feb. 28, 2013 (EP) .................................... 13157270

(51) Int. Cl.
*C07D 207/40* (2006.01)
*A01N 47/36* (2006.01)
*C07D 207/34* (2006.01)
*C07D 401/04* (2006.01)
*C07D 401/12* (2006.01)
*C07D 401/14* (2006.01)
*C07D 417/04* (2006.01)

(52) U.S. Cl.
CPC ........... *C07D 207/40* (2013.01); *A01N 47/36* (2013.01); *C07D 207/34* (2013.01); *C07D 401/04* (2013.01); *C07D 401/12* (2013.01); *C07D 401/14* (2013.01); *C07D 417/04* (2013.01)

(58) Field of Classification Search
CPC .... A01N 2300/00; A01N 43/16; A01N 43/90; A01N 43/08; A01N 43/38; A01N 43/12; A01N 33/12; A01N 37/46; A01N 43/40; A01N 57/20; A01N 27/00; A01N 37/42; A01N 37/50; A01N 43/653; A01N 43/82
See application file for complete search history.

(56) References Cited

FOREIGN PATENT DOCUMENTS

| EP | 2562171 A1 | 2/2013 | | |
|----|------------|--------|---|---|
| FR | WO2012/104538 A1 * | 8/2012 | ........... | C07D 401/12 |
| JP | EP2562171 A1 * | 2/2013 | ........... | C07D 307/60 |
| WO | 2012/043813 A1 | 4/2012 | | |

* cited by examiner

*Primary Examiner* — Audrea Buckley
(74) *Attorney, Agent, or Firm* — Brian D. McAlhaney

(57) ABSTRACT

The present invention relates to novel strigolactam derivatives, to processes and intermediates for preparing them, to plant growth regulator compositions comprising them and to methods of using them for controlling the growth of plants and/or promoting the germination of seeds.

15 Claims, No Drawings

PLANT GROWTH REGULATING COMPOUNDS

RELATED APPLICATION INFORMATION

This application is a 371 of International Application No. PCT/EP2014/053854, filed 27 Feb. 2014, which claims priority to 13157270.3, filed 28 Feb. 2013, the contents of all of which are incorporated herein by reference herein.

The present invention relates to novel heterocyclic derivatives, to processes and intermediates for preparing them, to plant growth regulator compositions comprising them and to methods of using them for controlling the growth of plants and/or promoting the germination of seeds.

Strigolactone derivatives are phytohormones with plant growth regulation and seed germination properties; they have been described, for example, in WO 2009/138655, WO 2010/125065, WO 2005/077177, WO 2006/098626, and Molecular Plant 2013, 6, 18-28. Strigolactone derivatives, like the synthetic analogue GR24, are known to have effect on the germination of parasitic weeds, such as *Orobanche* species. It is well established in the art that testing for germination of *Orobanche* seeds is a useful test to identify strigolactone analogues (for example, see Plant and Cell Physiology (2010), 51(7) p. 1095; and Organic & Biomolecular Chemistry (2009), 7(17), p. 3413).

Recently, simplified derivatives have been reported with strigolactone activity, as for example in WO 2011/125714 or in WO 2012/043813. These derivatives retain similar activity to GR-24 and natural strigolactones in biological assay on plants, inhibiting bud outgrowth or germination of parasitic weed seeds (Molecular Plant 2013, 6, 88-99).

The butenolide ring of strigolactone is considered an important part of the strigolactone compound. In the past, modification of this group has lead to a loss of activity on germination (Journal Agriculture and Food Chemistry 1997, 2284-2290) or loss of control on the plant architecture (Plant Physiol. 2012, 159, 1524-1544). Recently, it has also been proposed that an α/β hydrolase (D14 in rice or DAD2 in *petunia*) acts as the strigolactone receptor and that this protein hydrolyses the butenolide ring of strigolactones (Current Biology 2012, 22, 2032-2036 and Genes to Cell 2013, 18, 147-160)

Contrary to the teaching in the prior art, it has now surprisingly been found that certain heterocyclic derivatives with a modified butenolide ring have properties which are at least as good as strigolactone. The new compounds may result in improved plant growth properties, faster germination, earlier germination and/or reduced toxicity.

According to the present invention, there is provided a compound of Formula (I)

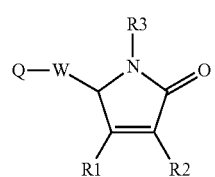

wherein
W is selected from O, S, SO or $SO_2$;
R1 and R2 are independently selected from H, C1-C6 alkyl, C1-C6 haloalkyl, halogen, C1-C6 alkoxy, aryloxy, C1-C6 alkylsulfinyl, C1-C6 alkylsulfonyl, C1-C6 alkylthio;
or R1 and R2 form a C5 or C6 cycloalkyl;
R3 is selected from H, C1-C6 alkyl (optionally substituted by one to five R4), hydroxyl, C1-C6 alkoxy, cyano, nitro, C1-C6 sulfonylalkyl, acetyl, C1-C6 alkoxycarbonyl, C3-C6 cycloalkyl (optionally substituted by R4), C2-C6 alkenyl (optionally substituted by one to five R4), C2-C6 alkynyl (optionally substituted by one to five R4), C3-C6 heterocyclyl (optionally substituted by one to five R4);
or R3 is selected from benzyl or aryl each optionally substituted with C1-C3 alkyl, C1-C3 alkoxy, C1-C3 alkylalkoxy, cyano, nitro, halogen or with C1-C3 haloalkyl;
wherein R4 is selected from halogen, C1-C3 alkyl, C1-C3 haloalkyl, C1-C3 alkoxy, cyano or nitro;
and Q is selected from one of (i) or (ii):

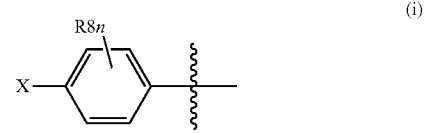

wherein X is selected from H, C1-C3 alkyl, halogen, C1-C3 alkoxy, C1-C3 alkoxyalkyl, C1-C3 haloalkyl, C1-C3 cyanoalkyl, cyano, nitro, C1-C3 alkylcarbonyl, C1-C3 alkoxycarbonyl, carboxyl, C1-C3 sulfonylalkyl, C2-C3 alkynyl, acetoxy, phenyl or phenyl substituted with C1-C3 alkyl, C1-C3 alkoxy, C1-C3 haloalkyl, C1-C3 alkylcyano or with cyano;
R8 is selected from C1-C3 alkyl, C1-C3 alkoxy, halogen, C1-C3 haloalkyl, cyano, and nitro; and
n is selected from 0 to 4;
ii)

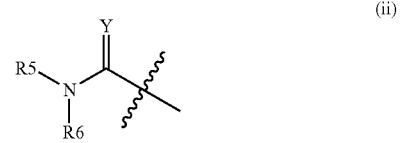

wherein Y is selected from O or S;
R5 is selected from hydrogen or C1-C6 alkyl;
R6 is selected from C1-C6 alkyl (optionally substituted with halogen), C1-C3 alkoxy, cyano, nitro; or
R6 is aryl or heteroaryl, each optionally substituted with R9; and
wherein R9 is selected from halogen, C1-C3 haloalkyl, C1-C3 alkyl, C1-C3 alkoxy, cyano or nitro;
or salts or N-oxides thereof;
with the provisos that:
a) when R1 and R2 form a C6 cycloalkyl, then R3 cannot be substituted phenyl; or
b) when R1 and R2 form a C6 cycloalkyl and Q is (ii), then R3 cannot be heteroaryl substituted or unsubstituted; or
c) when R1 and R2 are both methyl, W is O and Q is (ii), then R3 cannot be substituted heteroaryl or substituted phenyl or unsubstituted heteroaryl; or
d) when R1 and R2 are both methyl, W is O and Q is an unsubstituted phenyl, then R3 cannot be benzyl; or
e) when R1 and R2 are both methyl, W is S and Q is (i), then R3 cannot be benzyl, butyl, substituted heteroaryl or substituted phenyl; or f) when R1 and R2 are both chlorine, W is S and Q is an unsubstituted phenyl, then R3 cannot be 2,4-dimethoxybenzyl; or
g) when R1 and R2 are both hydrogen, W is S and Q is an unsubstituted phenyl, then R3 cannot be tertbutoxycarbonyl; or
h) when W is $SO_2$ and Q is (i), then R3 cannot be H or tertbutoxycarbonyl.

The compounds of Formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of Formula (I).

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$-$C_6$ alkyl groups, more preferably $C_1$-$C_4$ and most preferably $C_1$-$C_3$ alkyl groups.

Each alkenyl moiety either alone or as part of a larger group (such as alkenoxy, alkenoxycarbonyl, alkenylcarbonyl, alkyenlaminocarbonyl, dialkenylaminocarbonyl) is having at least one carbon-carbon double bond and is, for example, vinyl, allyl. The alkenyl groups are preferably $C_2$-$C_6$ alkenyl groups, more preferably $C_2$-$C_4$ alkenyl groups.

The term "alkenyl", as used herein, unless otherwise indicated, includes alkyl moieties having at least one carbon-carbon double bond wherein alkyl is as defined above The term "acetoxy" refers to —OC(=O)$CH_3$.

Each alkynyl moiety either alone or as part of a larger group (such as alkynoxy, alkynoxycarbonyl, alkynylcarbonyl, alkynylaminocarbonyl, dialkynylaminocarbonyl) is having at least one carbon-carbon triple bond and is, for example, ethynyl, propargyl. The alkynyl groups are preferably $C_2$-$C_6$ alkynyl groups, more preferably $C_2$-$C_4$ alkynyl groups. The term "alkynyl", as used herein, unless otherwise indicated, includes alkyl moieties having at least one carbon-carbon triple bond wherein alkyl is as defined above.

Halogen is fluorine (F), chlorine (Cl), bromine (Br) or iodine (I).

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Hydroxyalkyl groups are alkyl groups which are substituted with one or more hydroxyl group and are, for example, —$CH_2OH$, —$CH_2CH_2OH$ or —$CH(OH)CH_3$.

Alkoxyalkyl groups are —$(CH_2)_rO(CH_2)_sCH_3$ groups, wherein r is 1 to 6 and s is 1 to 5.

In the context of the present specification the term "aryl" refers to a ring system which may be mono-, bi- or tricyclic. Preferred aryl groups are monocyclic. Examples of such rings include phenyl, naphthalenyl, anthracenyl, indenyl or phenanthrenyl. Preferred aryl groups are monocyclic. A preferred aryl group is phenyl. Another preferred aryl group is benzyl and homobenzyl. "Benzyl" refers to —$CH_2C_6H_5$ and "homobenzyl" refers to —$(CH_2)_2C_6H_5$.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl ethynyl and propargyl.

Unless otherwise indicated, cycloalkyl may be mono- or bi-cyclic, may be optionally substituted by one or more $C_1$-$C_6$ alkyl groups, and preferably contain 3 to 7 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" is defined to include heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzo-furanyl, piperidinyl, 1,3-dioxolanyl, 1,3-dioxanyl, 4,5-dihydro-isoxazolyl, tetrahydrofuranyl and morpholinyl. In addition, the term "heterocyclyl" is defined to include "heterocycloalkyl" defined to be a non-aromatic monocyclic or polycyclic ring comprising carbon and hydrogen atoms and at least one heteroatom, preferably, 1 to 4 heteroatoms selected from nitrogen, oxygen, and sulfur such asoxetanyl or thietanyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl.

Preferred values of Y, W, R1, R2, R3, R4, R5, R6, R8, are, in any combination, as set out below.

W is preferably O or S.

R1 is preferably H, methyl, ethyl, halogen or methoxy; more preferably is R1 hydrogen or methyl.

R2 is preferably from H, methyl, ethyl, halogen or methoxy; more preferably is R2 hydrogen or methyl.

Or R1 and R2 form a C5 or C6 cycloalkyl; more preferably, R1 and R2 form a C6 cycloalkyl.

Preferably, R1 and R2 do not form a cycloalkyl. More preferably R1 and R2 are selected from hydrogen or methyl.

In one embodiment, one of R1 and R2 is hydrogen and the other is methyl. More preferably, R1 is hydrogen and R2 is methyl.

R3 is preferably selected from H, C1-C6 alkyl optionally substituted by one to five R4, hydroxyl, methoxy, ethoxy, cyano, acetyl, acetoxy, cyclopropyl optionally substituted with R4, C1-C6 alkenyl optionally substituted by one to five R4, C1-C6 alkynyl optionally substituted by one to five R4, heteroaryl optionally substituted with methyl, halogen or methoxy, benzyl optionally substituted with methyl, halogen or methoxy, phenyl optionally substituted with methyl, halogen or methoxy.

More preferably, R3 is hydrogen, methyl, ethyl, butyl, isopropyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl.

Each R4 is preferably independently halogen, methoxy or cyano.

More preferably, R4 is selected from fluorine, chlorine, methoxy and cyano.

In one embodiment, Q is selected from formula (i):

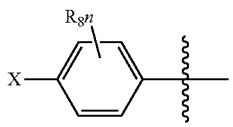

wherein X is preferably H, methyl, ethyl, iso-propyl, halogen, alkoxy, alkoxyalkyl, haloalkyl, cyano, nitro, acetylenyl, acetoxy or unsubstituted phenyl;

X is more preferably H, methyl, ethyl, chlorine, fluorine, bromine, trifluoromethyl, methoxymethyl, methoxyethyl, methoxy, ethoxy, cyano, nitro, acetylenyl, acetoxy, carboxyl, acetyl, methoxycarbonyl, or unsubstituted phenyl.

R8 is preferably methyl, ethyl, methoxy, ethoxy, chlorine, fluorine or bromine, haloalkyl, cyano or nitro.

R8 is more preferably methyl, methoxy, chlorine, fluorine or bromine, trifluoromethyl, cyano or nitro.

n is selected from 0 to 4. In certain embodiments, n is selected from 0, 1, or 2.

In another embodiment, Q is selected from formula (ii):

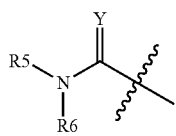

Y is preferably O.

R5 is preferably H or methyl.

More preferably, R5 is hydrogen;

R6 is preferably C1-C6 alkyl optionally substituted with halogen, or R6 is phenyl, benzyl, or homobenzyl or a heteroaryl each being optionally substituted with halogen, C1-C3 alkyl, C1-C3 haloalkyl, C1-C3 alkoxy, cyano or nitro.

More preferably, R6 is phenyl, benzyl, or homobenzyl each being optionally substituted with one or more of bromine, chlorine, fluorine, methyl, ethyl, iso-propyl, trifluoromethyl, methoxy, ethoxy, cyano and nitro.

Thus, in one embodiment of formula (I), when Q is selected from formula (i):

R1 is selected from H, methyl, ethyl, halogen or methoxy;

R2 is selected from H, methyl, ethyl, halogen or methoxy;

R3 is selected from H, C1-C6 alkyl optionally substituted by one to five R4, hydroxyl, methoxy, ethoxy, cyano, acetyl, acetoxy, cyclopropyl optionally substituted with R4, C1-C6 alkenyl optionally substituted by one to five R4, C1-C6 alkynyl optionally substituted by one to five R4, wherein each R4 is preferably independently halogen, methoxy or cyano;

X is selected from H, methyl, ethyl, iso-propyl, halogen, alkoxy, alkoxyalkyl, haloalkyl, cyano, nitro, acetylenyl, acetoxy or from unsubstituted phenyl;

R8 is preferably methyl, ethyl, methoxy, ethoxy, chlorine, fluorine, bromine, haloalkyl, cyano, and nitro;

n is selected from 0 to 4; and

W is O or S.

In a more preferred embodiment of formula (I) when Q is selected from formula (i):

R1 is selected from hydrogen or methyl;

R2 is selected from hydrogen or methyl;

R3 is selected from hydrogen, methyl, ethyl, butyl, iso-propyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;

X is selected from H, methyl, ethyl, chlorine, fluorine or bromine, trifluoromethyl, methoxymethyl, methoxyethyl, methoxy, ethoxy, cyano, nitro, acetylenyl, acetoxy or from unsubstituted phenyl;

R8 is selected from methyl, methoxy, chlorine, fluorine, bromine, trifluoromethyl, cyano or nitro;

n is selected from 0, 1, or 2; and

W is O or S

In another preferred embodiment of formula (I) when Q is selected from formula (i):

R1 and R2 are methyl;

R3 is selected from hydrogen, methyl, ethyl, butyl, iso-propyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;

X is selected from H, methyl, ethyl, chlorine, fluorine, bromine, trifluoromethyl, methoxymethyl, methoxyethyl, methoxy, ethoxy, cyano, nitro, acetylenyl, acetoxy or from unsubstituted phenyl;

R8 is selected from methyl, methoxy, chlorine, fluorine or bromine, trifluoromethyl, cyano, nitro;

n is selected from 0, 1, or 2; and

W is O.

In another preferred embodiment of formula (I), when Q is selected from formula (i) and R1 and R2 form a C6 cycloalkyl, preferably unsubstituted:

R3 is selected from H, C1-C6 alkyl optionally substituted by one to five R4, methoxy, ethoxy, cyano, acetyl, acetoxy, cyclopropyl optionally substituted with R4, C1-C6 alkenyl optionally substituted by one to five R4, C1-C6 alkynyl optionally substituted by one to five R4; wherein each R4 is preferably independently halogen, methoxy or cyano;

X is selected from H, methyl, ethyl, iso-propyl, halogen, alkoxy, alkoxyalkyl, haloalkyl, cyano, nitro, acetylenyl, acetoxy or from unsubstituted phenyl;

R8 is preferably methyl, ethyl, methoxy, ethoxy, chlorine, fluorine, bromine, haloalkyl, cyano and nitro;

n is selected from 0 to 4; and

W is O.

In a more preferred embodiment of formula (I), when Q is selected from formula (i) and R1 and R2 form an C6 cycloalkyl, preferably unsubstituted:

R3 is selected from hydrogen, methyl, ethyl, butyl, iso-propyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;

X is selected from H, methyl, ethyl, chlorine, fluorine, bromine, trifluoromethyl, methoxymethyl, methoxyethyl, methoxy, ethoxy, cyano, nitro, acetylenyl, acetoxy or from unsubstituted phenyl;

R8 is selected from methyl, methoxy, chlorine, fluorine or bromine, trifluoromethyl, cyano, nitro;

n is selected from 0, 1, or 2; and

W is O.

In another preferred embodiment of formula (I), when Q is selected from formula (ii):
R1 is selected from H, methyl, ethyl, halogen or methoxy;
R2 is selected from H, methyl, ethyl, halogen or methoxy;
R3 is selected from H, C1-C6 alkyl optionally substituted by one to five R4, hydroxyl, methoxy, ethoxy, cyano, acetyl, acetoxy, cyclopropyl optionally substituted with R4, C1-C6 alkenyl optionally substituted by one to five R4, C1-C6 alkynyl optionally substituted by one to five R4;
wherein each R4 is preferably independently halogen, methoxy or cyano;
R5 is selected from H or methyl;
R6 is selected from C1-C6 alkyl, optionally substituted with halogen, or R6 is phenyl, benzyl, or homobenzyl or a heteroaryl each being optionally substituted with halogen, C1-C3 alkyl, C1-C3 haloalkyl, C1-C3 alkoxy, cyano or with nitro;
W is O or S; and
Y is O or S.

In a more preferred embodiment of formula (I), when Q is selected from formula (ii):
R1 is selected from hydrogen or methyl;
R2 is selected from hydrogen or methyl;
R3 is selected from hydrogen, methyl, ethyl, butyl, isopropyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;
R5 is H;
R6 is selected from phenyl, benzyl, or homobenzyl or a heteroaryl each being optionally substituted with halogen, C1-C3 alkyl, C1-C3 haloalkyl, C1-C3 alkoxy, cyano or with nitro;
W is O or S; and
Y is O.

In another preferred embodiment of formula (I), when Q is selected from formula (ii):
R1 and R2 are methyl;
R3 is selected from hydrogen, methyl, ethyl, butyl, isopropyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;
R5 is H;
R6 is selected from phenyl, benzyl, or homobenzyl or a heteroaryl each being optionally substituted with halogen, C1-C3 alkyl, C1-C3 haloalkyl, C1-C3 alkoxy, cyano or with nitro;
W is O; and
Y is O.

In another preferred embodiment of formula (I), when Q is selected from formula (ii) and R1 and R2 form a C6 cycloalkyl, preferably unsubstituted:
R3 is selected from H, C1-C6 alkyl optionally substituted by one to five R4, methoxy, ethoxy, cyano, acetyl, acetoxy, cyclopropyl optionally substituted with R4, C1-C6 alkenyl optionally substituted by one to five R4, C1-C6 alkynyl optionally substituted by one to five R4;
wherein each R4 is preferably independently halogen, methoxy, cyano;
R5 is selected from H or methyl;
R6 is selected from C1-C6 alkyl, optionally substituted with halogen, or R6 is phenyl, benzyl, or homobenzyl or a heteroaryl each being optionally substituted with halogen, C1-C3 alkyl, C1-C3 haloalkyl, C1-C3 alkoxy, cyano or with nitro;
W is O; and
Y is O.

In another more preferred embodiment of formula (I), when Q is selected from formula (ii) and R1 and R2 form an C6 cycloalkyl, preferably unsubstituted:
R3 is selected from hydrogen, methyl, ethyl, butyl, isopropyl, trifluoromethyl trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl;
R5 is H;
R6 is selected from phenyl, benzyl, or homobenzyl or a heteroaryl each being optionally substituted with halogen, C1-C3 alkyl, C1-C3 haloalkyl, C1-C3 alkoxy, cyano or with nitro;
W is O; and
Y is O.

Table 1 below includes examples of compounds of Formula (Ia) wherein Q is formula (ii) and R1, R2, R3, R5, R6, Y and W are as defined below:

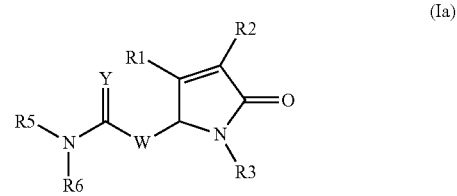

(Ia)

TABLE 1

| Compound | R1 | R2 | R3 | R5 | R6 | Y | W |
|---|---|---|---|---|---|---|---|
| 1.00 | H | Me | H | H | Bn | O | O |
| 1.01 | H | Me | Me | H | Bn | O | O |
| 1.02 | H | Me | OMe | H | Bn | O | O |
| 1.03 | H | Me | CH$_2$OMe | H | Bn | O | O |
| 1.04 | H | Me | cyclopropyl | H | Bn | O | O |
| 1.05 | H | Me | CH$_2$CF$_3$ | H | Bn | O | O |
| 1.06 | H | Me | CH$_2$CCH | H | Bn | O | O |
| 1.07 | H | Me | CH$_2$CHCH$_2$ | H | Bn | O | O |
| 1.08 | H | Me | Bn | H | Bn | O | O |
| 1.09 | H | Me | Ph | H | Bn | O | O |
| 1.10 | H | Me | Pyridine | H | Bn | O | O |
| 1.11 | H | Me | OEt | H | Bn | O | O |
| 1.12 | H | Me | CH(CH$_2$OCH$_2$) | H | Bn | O | O |
| 1.13 | H | Me | CH(CH$_2$SCH$_2$) | H | Bn | O | O |
| 1.14 | H | Me | CH(CH$_2$SO$_2$CH$_2$) | H | Bn | O | O |
| 1.15 | H | Me | CH$_2$CH$_2$OMe | H | Bn | O | O |
| 1.16 | H | Me | CH$_2$Me$_2$ | H | Bn | O | O |
| 1.17 | H | Me | COH | H | Bn | O | O |
| 1.18 | H | Me | COMe | H | Bn | O | O |
| 1.19 | Me | Me | H | H | Bn | O | O |
| 1.20 | Me | Me | Me | H | Bn | O | O |
| 1.21 | Me | Me | OMe | H | Bn | O | O |
| 1.22 | Me | Me | CH$_2$OMe | H | Bn | O | O |
| 1.23 | Me | Me | cyclopropyl | H | Bn | O | O |
| 1.24 | Me | Me | CH$_2$CF$_3$ | H | Bn | O | O |
| 1.25 | Me | Me | CH$_2$CCH | H | Bn | O | O |
| 1.26 | Me | Me | CH$_2$CHCH$_2$ | H | Bn | O | O |
| 1.30 | Me | Me | OEt | H | Bn | O | O |
| 1.31 | Me | Me | CH(CH$_2$OCH$_2$) | H | Bn | O | O |
| 1.32 | Me | Me | CH(CH$_2$SCH$_2$) | H | Bn | O | O |
| 1.33 | Me | Me | CH(CH$_2$SO$_2$CH$_2$) | H | Bn | O | O |
| 1.34 | Me | Me | CH$_2$CH$_2$OMe | H | Bn | O | O |
| 1.35 | Me | Me | CH$_2$Me$_2$ | H | Bn | O | O |
| 1.36 | Me | Me | COH | H | Bn | O | O |
| 1.37 | Me | Me | COMe | H | Bn | O | O |
| 1.38 | H | Me | H | H | Ph | O | O |
| 1.39 | H | Me | Me | H | Ph | O | O |
| 1.40 | H | Me | OMe | H | Ph | O | O |

TABLE 1-continued

| Compound | R1 | R2 | R3 | R5 | R6 | Y | W |
|---|---|---|---|---|---|---|---|
| 1.41 | H | Me | CH$_2$OMe | H | Ph | O | O |
| 1.42 | H | Me | cyclopropyl | H | Ph | O | O |
| 1.43 | H | Me | CH$_2$CF$_3$ | H | Ph | O | O |
| 1.44 | H | Me | CH$_2$CCH | H | Ph | O | O |
| 1.45 | H | Me | CH$_2$CHCH$_2$ | H | Ph | O | O |
| 1.46 | H | Me | Bn | H | Ph | O | O |
| 1.47 | H | Me | Ph | H | Ph | O | O |
| 1.48 | H | Me | Pyridine | H | Ph | O | O |
| 1.49 | H | Me | OEt | H | Ph | O | O |
| 1.50 | H | Me | CH(CH$_2$OCH$_2$) | H | Ph | O | O |
| 1.51 | H | Me | CH(CH$_2$SCH$_2$) | H | Ph | O | O |
| 1.52 | H | Me | CH(CH$_2$SO$_2$CH$_2$) | H | Ph | O | O |
| 1.53 | H | Me | CH$_2$CH$_2$OMe | H | Ph | O | O |
| 1.54 | H | Me | CH$_2$Me$_2$ | H | Ph | O | O |
| 1.55 | H | Me | COH | H | Ph | O | O |
| 1.56 | H | Me | COMe | H | Ph | O | O |
| 1.57 | Me | Me | H | H | Ph | O | O |
| 1.58 | Me | Me | Me | H | Ph | O | O |
| 1.59 | Me | Me | OMe | H | Ph | O | O |
| 1.60 | Me | Me | CH$_2$OMe | H | Ph | O | O |
| 1.61 | Me | Me | cyclopropyl | H | Ph | O | O |
| 1.62 | Me | Me | CH$_2$CF$_3$ | H | Ph | O | O |
| 1.63 | Me | Me | CH$_2$CCH | H | Ph | O | O |
| 1.64 | Me | Me | CH$_2$CHCH$_2$ | H | Ph | O | O |
| 1.65 | Me | Me | Bn | H | Ph | O | O |
| 1.68 | Me | Me | OEt | H | Ph | O | O |
| 1.69 | Me | Me | CH(CH$_2$OCH$_2$) | H | Ph | O | O |
| 1.70 | Me | Me | CH(CH$_2$SCH$_2$) | H | Ph | O | O |
| 1.71 | Me | Me | CH(CH$_2$SO$_2$CH$_2$) | H | Ph | O | O |
| 1.72 | Me | Me | CH$_2$CH$_2$OMe | H | Ph | O | O |
| 1.73 | Me | Me | CH$_2$Me$_2$ | H | Ph | O | O |
| 1.74 | Me | Me | COH | H | Ph | O | O |
| 1.75 | Me | Me | COMe | H | Ph | O | O |
| 1.76 | CH$_2$CH$_2$CH$_2$ | | H | H | Bn | O | O |
| 1.77 | CH$_2$CH$_2$CH$_2$ | | Me | H | Bn | O | O |
| 1.78 | CH$_2$CH$_2$CH$_2$ | | OMe | H | Bn | O | O |
| 1.79 | CH$_2$CH$_2$CH$_2$ | | CH$_2$OMe | H | Bn | O | O |
| 1.80 | CH$_2$CH$_2$CH$_2$ | | cyclopropyl | H | Bn | O | O |
| 1.81 | CH$_2$CH$_2$CH$_2$ | | CH$_2$CF$_3$ | H | Bn | O | O |
| 1.82 | CH$_2$CH$_2$CH$_2$ | | CH$_2$CCH | H | Bn | O | O |
| 1.83 | CH$_2$CH$_2$CH$_2$ | | CH$_2$CHCH$_2$ | H | Bn | O | O |
| 1.84 | CH$_2$CH$_2$CH$_2$ | | Bn | H | Bn | O | O |
| 1.85 | CH$_2$CH$_2$CH$_2$ | | Ph | H | Bn | O | O |
| 1.86 | CH$_2$CH$_2$CH$_2$ | | Pyridine | H | Bn | O | O |
| 1.87 | CH$_2$CH$_2$CH$_2$CH$_2$ | | H | H | Bn | O | O |
| 1.88 | CH$_2$CH$_2$CH$_2$CH$_2$ | | Me | H | Bn | O | O |
| 1.89 | CH$_2$CH$_2$CH$_2$CH$_2$ | | OMe | H | Bn | O | O |
| 1.90 | CH$_2$CH$_2$CH$_2$CH$_2$ | | CH$_2$OMe | H | Bn | O | O |
| 1.91 | CH$_2$CH$_2$CH$_2$CH$_2$ | | cyclopropyl | H | Bn | O | O |
| 1.92 | CH$_2$CH$_2$CH$_2$CH$_2$ | | CH$_2$CF$_3$ | H | Bn | O | O |
| 1.93 | CH$_2$CH$_2$CH$_2$CH$_2$ | | CH$_2$CCH | H | Bn | O | O |
| 1.94 | CH$_2$CH$_2$CH$_2$CH$_2$ | | CH$_2$CHCH$_2$ | H | Bn | O | O |
| 1.95 | CH$_2$CH$_2$CH$_2$CH$_2$ | | OEt | H | Bn | O | O |
| 1.96 | CH$_2$CH$_2$CH$_2$CH$_2$ | | CH(CH$_2$OCH$_2$) | H | Bn | O | O |
| 1.97 | CH$_2$CH$_2$CH$_2$CH$_2$ | | CH(CH$_2$SCH$_2$) | H | Bn | O | O |
| 1.98 | H | Me | H | H | Py | O | O |
| 1.99 | H | Me | Me | H | Py | O | O |
| 1.100 | H | Me | OMe | H | Py | O | O |
| 1.101 | H | Me | CH$_2$OMe | H | Py | O | O |
| 1.102 | H | Me | cyclopropyl | H | Py | O | O |
| 1.103 | H | Me | CH$_2$CF$_3$ | H | Py | O | O |
| 1.104 | H | Me | CH$_2$CCH | H | Py | O | O |
| 1.105 | H | Me | CH$_2$CHCH$_2$ | H | Py | O | O |
| 1.106 | H | Me | Bn | H | Py | O | O |
| 1.107 | H | Me | Ph | H | Py | O | O |
| 1.108 | H | Me | Pyridine | H | Py | O | O |
| 1.109 | H | Me | OEt | H | Py | O | O |
| 1.110 | H | Me | CH(CH$_2$OCH$_2$) | H | Py | O | O |
| 1.111 | H | Me | CH(CH$_2$SCH$_2$) | H | Py | O | O |
| 1.112 | H | Me | CH(CH$_2$SO$_2$CH$_2$) | H | Py | O | O |
| 1.113 | H | Me | CH$_2$CH$_2$OMe | H | Py | O | O |
| 1.114 | H | Me | CH$_2$Me$_2$ | H | Py | O | O |
| 1.115 | H | Me | COH | H | Py | O | O |
| 1.116 | H | Me | COMe | H | Py | O | O |
| 1.117 | H | Me | H | H | Bn | S | O |
| 1.118 | H | Me | Me | H | Bn | S | O |
| 1.119 | H | Me | OMe | H | Bn | S | O |
| 1.120 | H | Me | CH$_2$OMe | H | Bn | S | O |
| 1.121 | H | Me | cyclopropyl | H | Bn | S | O |
| 1.122 | H | Me | CH$_2$CF$_3$ | H | Bn | S | O |
| 1.123 | H | Me | CH$_2$CCH | H | Bn | S | O |
| 1.124 | H | Me | CH$_2$CHCH$_2$ | H | Bn | S | O |
| 1.125 | H | Me | Bn | H | Bn | S | O |
| 1.126 | H | Me | Ph | H | Bn | S | O |
| 1.127 | H | Me | Pyridine | H | Bn | S | O |
| 1.128 | H | Me | OEt | H | Bn | S | O |
| 1.129 | H | Me | CH(CH$_2$OCH$_2$) | H | Bn | S | O |
| 1.130 | H | Me | CH(CH$_2$SCH$_2$) | H | Bn | S | O |
| 1.131 | H | Me | CH(CH$_2$SO$_2$CH$_2$) | H | Bn | S | O |
| 1.132 | H | Me | CH$_2$CH$_2$OMe | H | Bn | S | O |
| 1.133 | H | Me | CH$_2$Me$_2$ | H | Bn | S | O |
| 1.134 | H | Me | COH | H | Bn | S | O |
| 1.135 | H | Me | COMe | H | Bn | S | O |
| 1.136 | H | Me | H | H | Bn | S | O |
| 1.137 | H | Me | Me | H | Bn | S | O |
| 1.138 | H | Me | OMe | H | Bn | S | O |
| 1.139 | H | Me | CH$_2$OMe | H | Bn | S | O |
| 1.140 | H | Me | cyclopropyl | H | Bn | S | O |

Table 2 below includes examples of compounds of Formula (Ib) wherein R1, R2, R3, X and W are as defined in the table below.

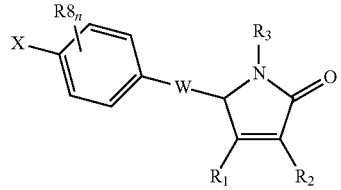

Ib

TABLE 2

| Compound | R1 | R2 | R3 | X | W | R8 | n |
|---|---|---|---|---|---|---|---|
| 2.00 | H | Me | H | Br | O | — | 0 |
| 2.01 | H | Me | Me | Br | O | — | 0 |
| 2.02 | H | Me | OMe | Br | O | — | 0 |
| 2.03 | H | Me | CH$_2$OMe | Br | O | — | 0 |
| 2.04 | H | Me | cyclopropyl | Br | O | — | 0 |
| 2.05 | H | Me | CH$_2$CF$_3$ | Br | O | — | 0 |
| 2.06 | H | Me | CH$_2$CCH | Br | O | — | 0 |
| 2.07 | H | Me | CH$_2$CHCH$_2$ | Br | O | — | 0 |
| 2.08 | H | Me | Bn | Br | O | — | 0 |
| 2.09 | H | Me | Ph | Br | O | — | 0 |
| 2.10 | H | Me | Pyridine | Br | O | — | 0 |
| 2.11 | H | Me | OEt | Br | O | — | 0 |
| 2.12 | H | Me | CH(CH$_2$OCH$_2$) | Br | O | — | 0 |
| 2.13 | H | Me | CH(CH$_2$SCH$_2$) | Br | O | — | 0 |
| 2.14 | H | Me | CH(CH$_2$SO$_2$CH$_2$) | Br | O | — | 0 |
| 2.15 | H | Me | CH$_2$CH$_2$OMe | Br | O | — | 0 |
| 2.16 | H | Me | CH$_2$Me$_2$ | Br | O | — | 0 |
| 2.17 | H | Me | COH | Br | O | — | 0 |
| 2.18 | H | Me | COMe | Br | O | — | 0 |
| 2.19 | Me | Me | H | Br | O | — | 0 |
| 2.20 | Me | Me | Me | Br | O | — | 0 |
| 2.21 | Me | Me | OMe | Br | O | — | 0 |
| 2.22 | Me | Me | CH$_2$OMe | Br | O | — | 0 |
| 2.23 | Me | Me | cyclopropyl | Br | O | — | 0 |
| 2.24 | Me | Me | CH$_2$CF$_3$ | Br | O | — | 0 |
| 2.25 | Me | Me | CH$_2$CCH | Br | O | — | 0 |
| 2.26 | Me | Me | CH$_2$CHCH$_2$ | Br | O | — | 0 |
| 2.27 | Me | Me | Bn | Br | O | — | 0 |
| 2.28 | Me | Me | Ph | Br | O | — | 0 |
| 2.29 | Me | Me | Pyridine | Br | O | — | 0 |
| 2.30 | Me | Me | OEt | Br | O | — | 0 |
| 2.31 | Me | Me | CH(CH$_2$OCH$_2$) | Br | O | — | 0 |
| 2.32 | Me | Me | CH(CH$_2$SCH$_2$) | Br | O | — | 0 |

TABLE 2-continued

| Compound | R1 | R2 | R3 | X | W | R8 | n |
|---|---|---|---|---|---|---|---|
| 2.33 | Me | Me | CH(CH$_2$SO$_2$CH$_2$) | Br | O | — | 0 |
| 2.34 | Me | Me | CH$_2$CH$_2$OMe | Br | O | — | 0 |
| 2.35 | Me | Me | CH$_2$Me$_2$ | Br | O | — | 0 |
| 2.36 | Me | Me | COH | Br | O | — | 0 |
| 2.37 | Me | Me | COMe | Br | O | — | 0 |
| 2.38 | H | Me | H | Cl | O | — | 0 |
| 2.39 | H | Me | Me | Cl | O | — | 0 |
| 2.40 | H | Me | OMe | Cl | O | — | 0 |
| 2.41 | H | Me | CH$_2$OMe | Cl | O | — | 0 |
| 2.42 | H | Me | cyclopropyl | Cl | O | — | 0 |
| 2.43 | H | Me | CH$_2$CF$_3$ | Cl | O | — | 0 |
| 2.44 | H | Me | CH$_2$CCH | Cl | O | — | 0 |
| 2.45 | H | Me | CH$_2$CHCH$_2$ | Cl | O | — | 0 |
| 2.46 | H | Me | Bn | Cl | O | — | 0 |
| 2.47 | H | Me | Ph | Cl | O | — | 0 |
| 2.48 | H | Me | Pyridine | Cl | O | — | 0 |
| 2.49 | H | Me | OEt | Cl | O | — | 0 |
| 2.50 | H | Me | CH(CH$_2$OCH$_2$) | Cl | O | — | 0 |
| 2.51 | H | Me | CH(CH$_2$SCH$_2$) | Cl | O | — | 0 |
| 2.52 | H | Me | CH(CH$_2$SO$_2$CH$_2$) | Cl | O | — | 0 |
| 2.53 | H | Me | CH$_2$CH$_2$OMe | Cl | O | — | 0 |
| 2.54 | H | Me | CH$_2$Me$_2$ | Cl | O | — | 0 |
| 2.55 | H | Me | COH | Cl | O | — | 0 |
| 2.56 | H | Me | COMe | Cl | O | — | 0 |
| 2.57 | Me | Me | H | Cl | O | — | 0 |
| 2.58 | Me | Me | Me | Cl | O | — | 0 |
| 2.59 | Me | Me | OMe | Cl | O | — | 0 |
| 2.60 | Me | Me | CH$_2$OMe | Cl | O | — | 0 |
| 2.61 | Me | Me | cyclopropyl | Cl | O | — | 0 |
| 2.62 | Me | Me | CH$_2$CF$_3$ | Cl | O | — | 0 |
| 2.63 | Me | Me | CH$_2$CCH | Cl | O | — | 0 |
| 2.64 | Me | Me | CH$_2$CHCH$_2$ | Cl | O | — | 0 |
| 2.65 | Me | Me | Bn | Cl | O | — | 0 |
| 2.66 | Me | Me | Ph | Cl | O | — | 0 |
| 2.67 | Me | Me | Pyridine | Cl | O | — | 0 |
| 2.68 | Me | Me | OEt | Cl | O | — | 0 |
| 2.69 | Me | Me | CH(CH$_2$OCH$_2$) | Cl | O | — | 0 |
| 2.70 | Me | Me | CH(CH$_2$SCH$_2$) | Cl | O | — | 0 |
| 2.71 | H | Me | H | Me | O | — | 0 |
| 2.72 | H | Me | Me | Me | O | — | 0 |
| 2.73 | H | Me | OMe | Me | O | — | 0 |
| 2.74 | H | Me | CH$_2$OMe | Me | O | — | 0 |
| 2.75 | H | Me | cyclopropyl | Me | O | — | 0 |
| 2.76 | H | Me | CH$_2$CF$_3$ | Me | O | — | 0 |
| 2.77 | H | Me | CH$_2$CCH | Me | O | — | 0 |
| 2.78 | H | Me | CH$_2$CHCH$_2$ | Me | O | — | 0 |
| 2.79 | H | Me | Bn | Me | O | — | 0 |
| 2.80 | H | Me | Ph | Me | O | — | 0 |
| 2.81 | H | Me | Pyridine | Me | O | — | 0 |
| 2.82 | H | Me | OEt | Me | O | — | 0 |
| 2.83 | H | Me | CH(CH$_2$OCH$_2$) | Me | O | — | 0 |
| 2.84 | H | Me | CH(CH$_2$SCH$_2$) | Me | O | — | 0 |
| 2.85 | H | Me | CH(CH$_2$SO$_2$CH$_2$) | Me | O | — | 0 |
| 2.86 | H | Me | CH$_2$CH$_2$OMe | Me | O | — | 0 |
| 2.87 | H | Me | CH$_2$Me$_2$ | Me | O | — | 0 |
| 2.88 | H | Me | COH | Me | O | — | 0 |
| 2.89 | H | Me | COMe | Me | O | — | 0 |
| 2.90 | Me | Me | H | Me | O | — | 0 |
| 2.91 | Me | Me | Me | Me | O | — | 0 |
| 2.92 | Me | Me | OMe | Me | O | — | 0 |
| 2.93 | Me | Me | CH$_2$OMe | Me | O | — | 0 |
| 2.94 | Me | Me | cyclopropyl | Me | O | — | 0 |
| 2.95 | Me | Me | CH$_2$CF$_3$ | Me | O | — | 0 |
| 2.96 | Me | Me | CH$_2$CCH | Me | O | — | 0 |
| 2.97 | Me | Me | CH$_2$CHCH$_2$ | Me | O | — | 0 |
| 2.98 | Me | Me | Bn | Me | O | — | 0 |
| 2.99 | Me | Me | Ph | Me | O | — | 0 |
| 2.100 | Me | Me | Pyridine | Me | O | — | 0 |
| 2.101 | Me | Me | OEt | Me | O | — | 0 |
| 2.102 | Me | Me | CH(CH$_2$OCH$_2$) | Me | O | — | 0 |
| 2.103 | Me | Me | CH(CH$_2$SCH$_2$) | Me | O | — | 0 |
| 2.104 | Me | Me | CH(CH$_2$SO$_2$CH$_2$) | Me | O | — | 0 |
| 2.105 | Me | Me | CH$_2$CH$_2$OMe | Me | O | — | 0 |
| 2.106 | Me | Me | CH$_2$Me$_2$ | Me | O | — | 0 |
| 2.107 | Me | Me | COH | Me | O | — | 0 |
| 2.108 | Me | Me | COMe | Me | O | — | 0 |
| 2.109 | H | Me | H | Me | O | Me | 1 |
| 2.110 | H | Me | Me | Me | O | Me | 1 |
| 2.111 | H | Me | OMe | Me | O | Me | 1 |
| 2.112 | H | Me | CH$_2$OMe | Me | O | Me | 1 |
| 2.113 | H | Me | cyclopropyl | Me | O | Me | 1 |
| 2.114 | H | Me | CH$_2$CF$_3$ | Me | O | Me | 1 |
| 2.115 | H | Me | CH$_2$CCH | Me | O | Me | 1 |
| 2.116 | H | Me | CH$_2$CHCH$_2$ | Me | O | Me | 1 |
| 2.117 | H | Me | Bn | Me | O | Me | 1 |
| 2.118 | H | Me | Ph | Me | O | Me | 1 |
| 2.119 | H | Me | Pyridine | Me | O | Me | 1 |
| 2.120 | H | Me | OEt | Me | O | Me | 1 |
| 2.121 | H | Me | CH(CH$_2$OCH$_2$) | Me | O | Me | 1 |
| 2.122 | H | Me | CH(CH$_2$SCH$_2$) | Me | O | Me | 1 |
| 2.123 | H | Me | CH(CH$_2$SO$_2$CH$_2$) | Me | O | Me | 1 |
| 2.124 | H | Me | CH$_2$CH$_2$OMe | Me | O | Me | 1 |
| 2.125 | H | Me | CH$_2$Me$_2$ | Me | O | Me | 1 |
| 2.126 | H | Me | COH | Me | O | Me | 1 |
| 2.127 | H | Me | COMe | Me | O | Me | 1 |
| 2.128 | Me | Me | H | Me | O | Me | 1 |
| 2.129 | Me | Me | Me | Me | O | Me | 1 |
| 2.130 | Me | Me | OMe | Me | O | Me | 1 |
| 2.131 | Me | Me | CH$_2$OMe | Me | O | Me | 1 |
| 2.132 | Me | Me | cyclopropyl | Me | O | Me | 1 |
| 2.133 | Me | Me | CH$_2$CF$_3$ | Me | O | Me | 1 |
| 2.134 | Me | Me | CH$_2$CCH | Me | O | Me | 1 |
| 2.135 | Me | Me | CH$_2$CHCH$_2$ | Me | O | Me | 1 |
| 2.136 | Me | Me | Bn | Me | O | Me | 1 |
| 2.137 | Me | Me | Ph | Me | O | Me | 1 |
| 2.138 | Me | Me | Pyridine | Me | O | Me | 1 |
| 2.139 | Me | Me | OEt | Me | O | Me | 1 |
| 2.140 | H | Me | H | Br | S | — | 0 |
| 2.141 | H | Me | Me | Br | S | — | 0 |
| 2.142 | H | Me | OMe | Br | S | — | 0 |
| 2.143 | H | Me | CH$_2$OMe | Br | S | — | 0 |
| 2.144 | H | Me | cyclopropyl | Br | S | — | 0 |
| 2.145 | H | Me | CH$_2$CF$_3$ | Br | S | — | 0 |
| 2.146 | H | Me | CH$_2$CCH | Br | S | — | 0 |
| 2.147 | H | Me | CH$_2$CHCH$_2$ | Br | S | — | 0 |
| 2.148 | H | Me | Bn | Br | S | — | 0 |
| 2.149 | H | Me | Ph | Br | S | — | 0 |
| 2.150 | H | Me | Pyridine | Br | S | — | 0 |
| 2.151 | H | Me | OEt | Br | S | — | 0 |
| 2.152 | H | Me | CH(CH$_2$OCH$_2$) | Br | S | — | 0 |
| 2.153 | H | Me | CH(CH$_2$SCH$_2$) | Br | S | — | 0 |
| 2.154 | H | Me | CH(CH$_2$SO$_2$CH$_2$) | Br | S | — | 0 |
| 2.155 | H | Me | CH$_2$CH$_2$OMe | Br | S | — | 0 |
| 2.156 | H | Me | CH$_2$Me$_2$ | Br | S | — | 0 |
| 2.157 | H | Me | COH | Br | S | — | 0 |
| 2.158 | H | Me | COMe | Br | S | — | 0 |
| 2.159 | Me | Me | H | Br | S | — | 0 |
| 2.160 | Me | Me | Me | Br | S | — | 0 |
| 2.161 | Me | Me | OMe | Br | S | — | 0 |
| 2.162 | Me | Me | CH$_2$OMe | Br | S | — | 0 |
| 2.163 | Me | Me | cyclopropyl | Br | S | — | 0 |
| 2.164 | Me | Me | CH$_2$CF$_3$ | Br | S | — | 0 |
| 2.165 | Me | Me | CH$_2$CCH | Br | S | — | 0 |
| 2.166 | Me | Me | CH$_2$CHCH$_2$ | Br | S | — | 0 |
| 2.167 | Me | Me | Bn | Br | S | — | 0 |
| 2.168 | Me | Me | Ph | Br | S | — | 0 |
| 2.169 | Me | Me | Pyridine | Br | S | — | 0 |
| 2.170 | Me | Me | OEt | Br | S | — | 0 |
| 2.171 | Me | Me | CH(CH$_2$OCH$_2$) | Br | S | — | 0 |
| 2.172 | Me | Me | CH(CH$_2$SCH$_2$) | Br | S | — | 0 |
| 2.173 | Me | Me | CH(CH$_2$SO$_2$CH$_2$) | Br | S | — | 0 |
| 2.174 | Me | Me | CH$_2$CH$_2$OMe | Br | S | — | 0 |
| 2.175 | Me | Me | CH$_2$Me$_2$ | Br | S | — | 0 |
| 2.176 | Me | Me | COH | Br | S | — | 0 |
| 2.177 | Me | Me | COMe | Br | S | — | 0 |
| 2.178 | H | Me | H | Cl | S | — | 0 |
| 2.179 | H | Me | Me | Cl | S | — | 0 |
| 2.180 | H | Me | OMe | Cl | S | — | 0 |
| 2.181 | H | Me | CH$_2$OMe | Cl | S | — | 0 |
| 2.182 | H | Me | cyclopropyl | Cl | S | — | 0 |
| 2.183 | H | Me | CH$_2$CF$_3$ | Cl | S | — | 0 |
| 2.184 | H | Me | CH$_2$CCH | Cl | S | — | 0 |
| 2.185 | H | Me | CH$_2$CHCH$_2$ | Cl | S | — | 0 |
| 2.186 | H | Me | Bn | Cl | S | — | 0 |
| 2.187 | H | Me | Ph | Cl | S | — | 0 |
| 2.188 | H | Me | Pyridine | Cl | S | — | 0 |

TABLE 2-continued

| Compound | R1 | R2 | R3 | X | W | R8 | n |
|---|---|---|---|---|---|---|---|
| 2.189 | H | Me | OEt | Cl | S | — | 0 |
| 2.190 | H | Me | CH(CH$_2$OCH$_2$) | Cl | S | — | 0 |
| 2.191 | H | Me | CH(CH$_2$SCH$_2$) | Cl | S | — | 0 |
| 2.192 | H | Me | CH(CH$_2$SO$_2$CH$_2$) | Cl | S | — | 0 |
| 2.193 | H | Me | CH$_2$CH$_2$OMe | Cl | S | — | 0 |
| 2.194 | H | Me | CH$_2$Me$_2$ | Cl | S | — | 0 |
| 2.195 | H | Me | COH | Cl | S | — | 0 |
| 2.196 | H | Me | COMe | Cl | S | — | 0 |
| 2.197 | Me | Me | H | Cl | S | — | 0 |
| 2.198 | Me | Me | Me | Cl | S | — | 0 |
| 2.199 | Me | Me | OMe | Cl | S | — | 0 |
| 2.200 | Me | Me | CH$_2$OMe | Cl | S | — | 0 |
| 2.201 | Me | Me | cyclopropyl | Cl | S | — | 0 |
| 2.202 | Me | Me | CH$_2$CF$_3$ | Cl | S | — | 0 |
| 2.203 | Me | Me | CH$_2$CCH | Cl | S | — | 0 |
| 2.204 | Me | Me | CH$_2$CHCH$_2$ | Cl | S | — | 0 |
| 2.205 | Me | Me | Bn | Cl | S | — | 0 |
| 2.206 | Me | Me | Ph | Cl | S | — | 0 |
| 2.207 | Me | Me | Pyridine | Cl | S | — | 0 |
| 2.208 | Me | Me | OEt | Cl | S | — | 0 |
| 2.209 | Me | Me | CH(CH$_2$OCH$_2$) | Cl | S | — | 0 |
| 2.210 | Me | Me | CH(CH$_2$SCH$_2$) | Cl | S | — | 0 |
| 2.211 | H | Me | H | Me | S | — | 0 |
| 2.212 | H | Me | Me | Me | S | — | 0 |
| 2.213 | H | Me | OMe | Me | S | — | 0 |
| 2.214 | H | Me | CH$_2$OMe | Me | S | — | 0 |
| 2.215 | H | Me | cyclopropyl | Me | S | — | 0 |
| 2.216 | H | Me | CH$_2$CF$_3$ | Me | S | — | 0 |
| 2.217 | H | Me | CH$_2$CCH | Me | S | — | 0 |
| 2.218 | H | Me | CH$_2$CHCH$_2$ | Me | S | — | 0 |
| 2.219 | H | Me | Bn | Me | S | — | 0 |
| 2.220 | H | Me | Ph | Me | S | — | 0 |
| 2.221 | H | Me | Pyridine | Me | S | — | 0 |
| 2.222 | H | Me | OEt | Me | S | — | 0 |
| 2.223 | H | Me | CH(CH$_2$OCH$_2$) | Me | S | — | 0 |
| 2.224 | H | Me | CH(CH$_2$SCH$_2$) | Me | S | — | 0 |
| 2.225 | H | Me | CH(CH$_2$SO$_2$CH$_2$) | Me | S | — | 0 |
| 2.226 | H | Me | CH$_2$CH$_2$OMe | Me | S | — | 0 |
| 2.227 | H | Me | CH$_2$Me$_2$ | Me | S | — | 0 |
| 2.228 | H | Me | COH | Me | S | — | 0 |
| 2.229 | H | Me | COMe | Me | S | — | 0 |
| 2.230 | Me | Me | H | Me | S | — | 0 |
| 2.231 | Me | Me | Me | Me | S | — | 0 |
| 2.232 | Me | Me | OMe | Me | S | — | 0 |
| 2.233 | Me | Me | CH$_2$OMe | Me | S | — | 0 |
| 2.234 | Me | Me | cyclopropyl | Me | S | — | 0 |
| 2.235 | Me | Me | CH$_2$CF$_3$ | Me | S | — | 0 |
| 2.236 | Me | Me | CH$_2$CCH | Me | S | — | 0 |
| 2.237 | Me | Me | CH$_2$CHCH$_2$ | Me | S | — | 0 |
| 2.238 | Me | Me | Bn | Me | S | — | 0 |
| 2.239 | Me | Me | Ph | Me | S | — | 0 |
| 2.240 | Me | Me | Pyridine | Me | S | — | 0 |
| 2.241 | Me | Me | OEt | Me | S | — | 0 |
| 2.242 | Me | Me | CH(CH$_2$OCH$_2$) | Me | S | — | 0 |
| 2.243 | Me | Me | CH(CH$_2$SCH$_2$) | Me | S | — | 0 |
| 2.244 | Me | Me | CH(CH$_2$SO$_2$CH$_2$) | Me | S | — | 0 |
| 2.245 | Me | Me | CH$_2$CH$_2$OMe | Me | S | — | 0 |
| 2.246 | Me | Me | CH$_2$Me$_2$ | Me | S | — | 0 |
| 2.247 | Me | Me | COH | Me | S | — | 0 |
| 2.248 | Me | Me | COMe | Me | S | — | 0 |
| 2.249 | H | Me | H | Br | S | — | 0 |

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound of Formula (I) and an agriculturally acceptable formulation adjuvant. The present invention further provides a plant growth regulator composition consisting essentially of a plant growth regulation compound of Formula (I) and an agriculturally acceptable formulation adjuvant. The present invention further provides a plant growth regulator composition consisting of a plant growth regulation compound of Formula (I) and an agriculturally acceptable formulation adjuvant. The present invention further provides a seed germination promoter composition comprising a seed germination promoter compound of Formula (I) and an agriculturally acceptable formulation adjuvant. The present invention further provides a seed germination promoter composition consisting essentially of a seed germination promoter compound of Formula (I) and an agriculturally acceptable formulation adjuvant. The present invention further provides a seed germination promoter composition consisting of a seed germination promoter compound of Formula (I) and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of Formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of Formula (I) or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula (I) may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula (I) according to the invention are generally applied at a rate of from 1 to 2000 g/ha, especially from 5 to 1000 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination. Thus, the invention also covers a method for controlling weeds comprising applying to a locus containing weed seeds a seed germination promoting amount of a composition or a compound according to the invention, allowing the seeds to germinate, and then applying to the locus a post-emergence herbicide.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO 02/46387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Compounds and compositions of the present invention may be applied in combination with other active ingredients or products for use in agriculture, including insecticides, fungicides, herbicides, plant growth regulators, crop enhancing compounds, nutrients and biologicals. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops.

The compounds of the invention may be made by the following methods.

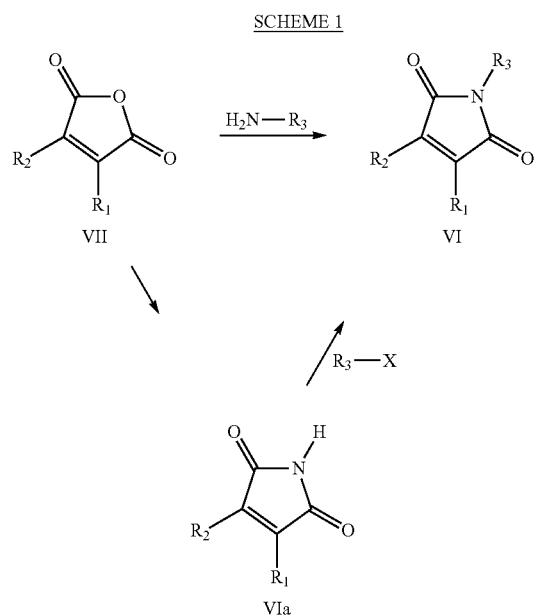

Compounds of formula (VI) may be prepared (VII) by reaction with an amine of formula R3NH$_2$ or its corresponding salt by heating in an alcoholic solvent.

Alternatively, compounds of formula VI can be prepared from compounds of formula VIa by reaction with an alkylating agent of formula R3X wherein X is a leaving group such as halogen or tosyl, in the presence of a base such as potassium carbonate, eventually in the presence of a catalyst such as potassium iodide.

Alternatively, compounds of formula VI can be prepared from compounds of formula VIa by reaction with a compound of formula R3X wherein X is an alkoxy group in the presence of a Lewis acid such as tin tetrachloride or boron trifluoride.

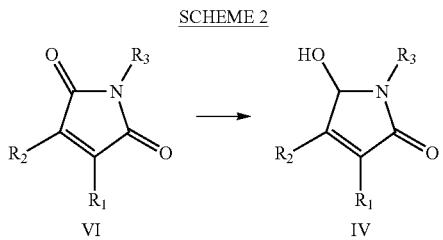

Compounds of Formula (IV) may be prepared from compounds of Formula (VI) by reaction with a reducing agent such as diisopropylaluminium hydride, sodium cyanoborohydride or sodium borohydride, optionally in the presence of a Lewis acid such as cerium trichloride. Similar reactions have been reported for example in J. Chem. Soc., Perkin Trans. 1, 2002, 707-709.

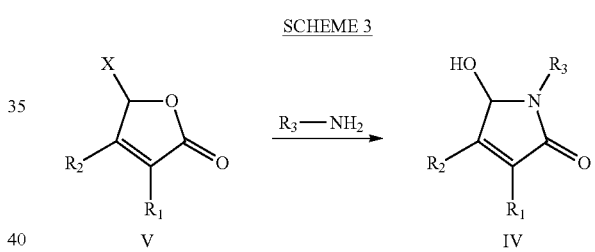

Compounds of formula (IV) may also be prepared from compounds of formula (V) by reaction with an amine of formula R3NH$_2$ or its corresponding hydrochloric salt, in the presence or not of a base and in an alcoholic solvent such as methanol or ethanol. Similar reactions have been described in Synthesis 1973, pages 167-168 or in Heterocycles, 1983, pages 1761-1767.

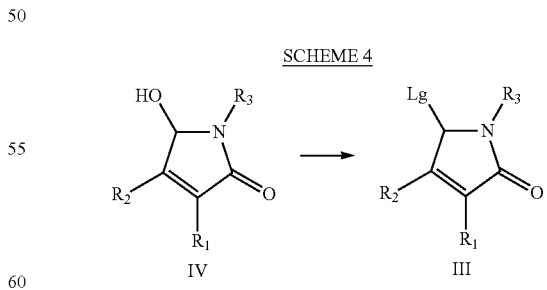

Compounds of formula (III) wherein Lg is a leaving group such as halogen may be prepared from compounds of formula (IV) by reaction with a chlorinating agent, such as thionyl chloride, phosgene or 1-chloro-N,N,2-trimethyl-1-propenylamine or a brominating agent such as PBr$_3$ or thionylbromide.

SCHEME 5

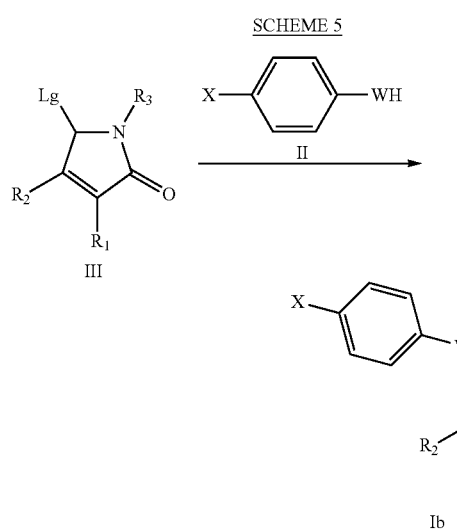

Compounds of formula (Ib) may be prepared from compounds of formula (III) by reaction with a compound of formula II in the presence of a base such as potassium carbonate. The reaction can alternatively be conducted in a biphasic mixture in the presence or not of a catalyst, such as tetrabutylammonium bromide.

SCHEME 6

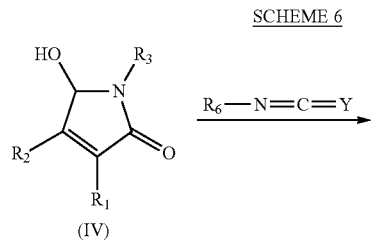

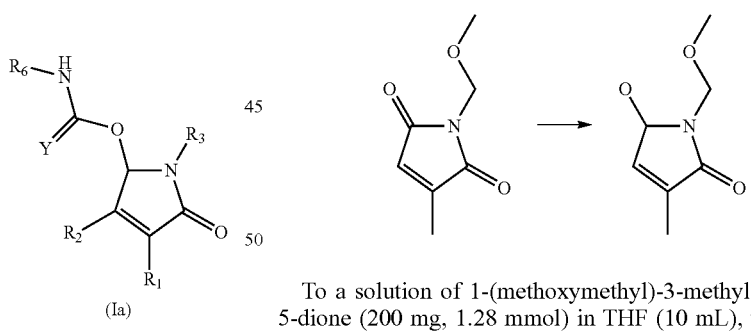

Compounds of Formula (Ia) may be prepared from a compound of Formula (IV) by reaction with a compound of isocyanate or formula R6NCY in the presence of a base such as triethylamine.

EXAMPLES

The following abbreviations are used throughout this section: s=singlet; bs=broad singlet; d=doublet; dd=double doublet; dt=double triplet; t=triplet, tt=triple triplet, q=quartet, m=multiplet; Me=methyl; Et=ethyl; Pr=propyl; Bu=butyl; Mp=melting point; DMF=N, N-dimethylformamide, THF=tetrahydrofuran.

Example 1

Step 1: 1-(methoxymethyl)-3-methyl-pyrrole-2,5-dione

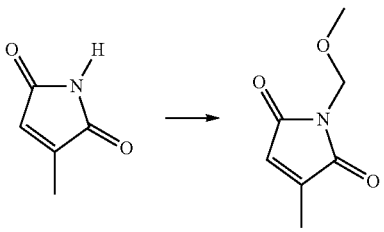

To a solution of 3-methylpyrrole-2,5-dione (4.50 mmol, 0.500 g, as prepared in European Journal of Organic Chemistry 2008, 9, 1511-1516) in dimethoxymethane (20 mL) under nitrogen was added slowly tin(IV) chloride (5.40 mmol, 0.632 mL). The reaction mixture was heated to 40° C. for 5 h and then cooled down to room temperature. The reaction mixture was then carefully neutralized with a saturated solution of potassium carbonate and extracted with ethyl acetate (3×20 mL). The organic phase was dried and evaporated giving the title compound as a white solid (657 mg, 94%). $^1$H NMR (400 MHz, CDCl$_3$) δ: 6.44 (1H, s), 4.89 (2H, s), 3.35 (3H, s), 2.13 (3H, s).

Step 2: 2-hydroxy-1-(methoxymethyl)-4-methyl-2H-pyrrol-5-one (II-1)

To a solution of 1-(methoxymethyl)-3-methyl-pyrrole-2,5-dione (200 mg, 1.28 mmol) in THF (10 mL), was added at −78° C. and under nitrogen diisopropyl aluminium hydride (1 M in dichloromethane, 1.54 mmol, 1.54 mL). The solution was stirred at −78° C. for 2 h and the reaction was then quenched a saturated solution of Rochelle's salt. Then it was extracted with ethyl acetate (3×30 mL) and washed with a saturated solution of Rochelle's salt and brine. The organic phase was dried and evaporated to give a brown oil, which was further purified by flash chromatography (20% to 100% ethyl acetate in cyclohexane). The desired product was obtained as a colourless oil 2-hydroxy-1-(methoxymethyl)-4-methyl-2H-pyrrol-5-one II-1 (28%, 57 mg); %). 1H NMR (400 MHz, CDCl$_3$) δ: 6.65 (1H, s), 5.50 (1H, d), 4.90 (1H, d), 4.73 (1H, d), 3.97 (1H, d), 3.33 (3H, s), 1.90 (3H, s).

A similar procedure was used to prepare compounds:

2-hydroxy-1,4-dimethyl-2H-pyrrol-5-one II-2; $^1$H NMR (400 MHz, CDCl$_3$) δ: 6.54 (1H, s), 5.16 (1H, d), 3.86 (1H, d), 2.91 (3H, s), 1.83 (3H, s).

2-hydroxy-1-phenyl-2H-pyrrol-5-one II-9; $^1$H NMR (400 MHz, CHLOROFORM-d) δ: 1.90 (s, 3H), 2.72 (d, 1H), 5.85 (d, 1H), 6.68 (t, 1H), 7.18 (d, 1H), 7.39 (t, 2H), 7.71 (d, 2H)

2-hydroxy-1-(3-pyridyl)-2H-pyrrol-5-one II-10; $^1$H NMR (400 MHz, DMSO-d$_6$) δ: 1.86 (t, 3H), 6.00 (d, 1H), 6.52 (d, 1H), 6.93 (s, 1H), 7.36-7.47 (m, 1H), 8.08 (dd, 1H), 8.33 (dd, 1H) 8.90 (s, 1H).

2-hydroxy-1-(2-thiazoyl)-2H-pyrrol-5-one II-11; $^1$H NMR (400 MHz, CHLOROFORM-d) δ: 2.15-2.25 (s, 3H), 5.25 (s, 1H), 6.02 (s, 1H), 6.06 (s, 1H), 6.98 (d, 1H), 7.42 (d, 1H).

Step 3: [1-(methoxymethyl)-4-methyl-5-oxo-2H-pyrrol-2-yl]N-benzylcarbamate (Ia-1)

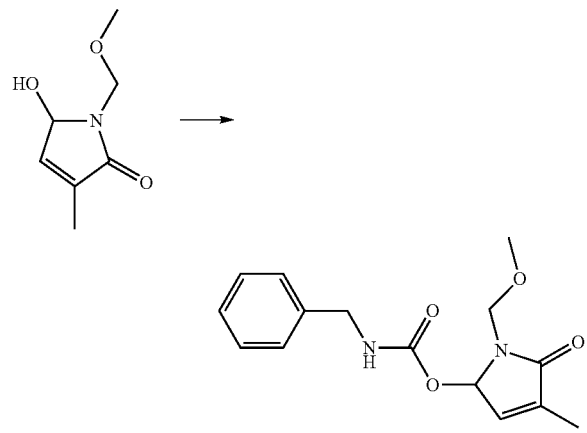

To a solution of 2-hydroxy-1-(methoxymethyl)-4-methyl-2H-pyrrol-5-one (57 mg, 0.362 mmol) in diisopropylether (4 mL) was added triethylamine (51 mL, 0.362 mmol) and then benzylisocyanate (0.362 mmol, 0.045 mL). The reaction was stirred overnight at room temperature. The reaction was quenched with saturated ammonium chloride and extracted with ethyl acetate. The combined organic layers were washed with brine, dried and concentrated. The residue was purified by flash chromatography (20% to 100% ethyl acetate in cyclohexane) to give [1-(methoxymethyl)-4-methyl-5-oxo-2H-pyrrol-2-yl]N-benzylcarbamate Ia-1 (54%, 57 mg). $^1$H NMR (400 MHz, CDCl$_3$) δ: 7.32-7.23 (5H, m), 6.64 (1H, s), 6.53 (1H, s), 5.49 (1H, m), 4.89 (1H, d), 4.69 (1H, d), 4.39 (2H, m), 3.26 (3H, s), 1.91 (3H, s).

A similar procedure was used to prepare compounds:

(1,4-dimethyl-5-oxo-2H-pyrrol-2-yl) N-benzylcarbamate Ia-2; Mp 106° C.; $^1$H NMR (400 MHz, CDCl$_3$) δ: 7.35-7.25 (5H, m), 6.51 (1H, s), 6.26 (1H, s), 5.75 (1H, brs), 4.39 (2H, d), 2.88 (3H, s), 1.88 (3H, s).

(1-phenyl-4-methyl-5-oxo-2H-pyrrol-2-yl) N-benzylcarbamate Ia-7; 1H NMR (400 MHz, CDCl$_3$) δ: 7.54 (d, 2H), 7.15-7.39 (m, 8H), 7.00 (s, 1H), 6.71-6.74 (m, 1H), 5.19 (s, 1H), 4.34 (dd, 2H), 1.96 (s, 3H).

(1-(3-pyridyl)-4-methyl-5-oxo-2H-pyrrol-2-yl) N-benzylcarbamate Ia-8; $^1$H NMR (400 MHz, DMSO-d$_6$) δ: 1.90 (m, 3H), 4.16 (m, 2H), 7.06-7.18 (m, 4H), 7.19-7.34 (m, 3H), 7.45 (dd, 1H), 7.89-7.97 (m, 1H), 8.04 (t, 1H), 8.42 (dd, 1H), 8.77 (d, 1H).

(1-(2-thiazoyl)-4-methyl-5-oxo-2H-pyrrol-2-yl) N-benzylcarbamate Ia-9; $^1$H NMR (400 MHz, CDCl$_3$) δ: 2.08-2.23 (s, 3H), 4.39 (dd, 1H), 4.54-4.68 (dd, 1H), 5.21 (m, 1H), 6.09 (m, 1H), 6.92-7.03 (d, 1H), 7.28-7.39 (m, 6H), 7.42 (d, 1H).

Example 2

Step 1:
1,2a,7,7a-tetrahydro-2H-cyclobut[a]thioinden-2-one II-3

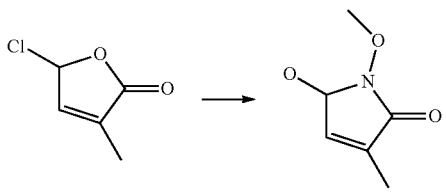

To a solution of 2-chloro-4-methyl-2H-furan-5-one (prepared according to Johnson & all, *J.C.S. Perkin I*, 1981, 1734-1743, 200 mg, 1.50 mmol) in methanol (8 mL) was added methoxyalmine hydrochloride (25 mass % in water, 1.88 mmol, 0.57 mL) and sodium acetate (125 mg, 1.50 mmol). The reaction mixture was stirred for 4 h and another equivalent of methoxylamine hydrochloride and sodium acetate were added and same again after 7 h. The reaction mixture was stirred for another 12 h. Brine was added and the reaction mixture was extracted with ethyl acetate. The organic phase was dried, evaporated and purified by flash chromatography (20% to 100% ethyl acetate in cyclohexane) to give the title compound II-3 (103 mg, 47%). $^1$H NMR (400 MHz, CDCl$_3$) δ: 6.47 (1H, s), 5.47 (1H, s), 3.93 (3H, s), 1.91 (3H, s).

A similar procedure was used to prepare compounds:

(1-benzyl-2-hydroxy-4-methyl-2H-pyrrol-5-one II-4; $^1$H NMR (400 MHz, CDCl$_3$) δ: 7.34-7.20 (5H, m), 6.54 (1H, s), 5.16 (1H, d), 4.94 (1H, d), 4.30 (1H, d), 2.38 (1H, d), 1.91 (3H, s).

1-cyclopropyl-2-(cyclopropylamino)-4-methyl-2H-pyrrol-5-one II-5; $^1$H NMR (400 MHz, CDCl$_3$) δ: 6.49 (1H, s), 5.22 (1H, brs), 3.61 (1H, brs), 2.61 (1H, m), 1.83 (3H, s), 1.01-0.66 (4H, m).

2-hydroxy-4-methyl-1-prop-2-ynyl-2H-pyrrol-5-one II-6; $^1$H NMR (400 MHz, CDCl$_3$) δ: 6.65 (1H, s), 5.52 (1H, d), 4.53 (1H, d), 4.02 (1H, d), 2.27 (1H, s), 2.20 (1H, d), 1.94 (3H, s).

2-hydroxy-1-isopropyl-4-methyl-2H-pyrrol-5-one II-7; $^1$H NMR (400 MHz, CDCl$_3$) δ: 6.50 (1H, s), 5.41 (1H, d), 4.24 (1H, m), 2.06 (1H, d), 1.88 (3H, s), 1.34 (6H, m).

2-hydroxy-4-methyl-1-(2,2,2-trifluoroethyl)-2H-pyrrol-5-one II-8; 4-methyl-1-(2,2,2-trifluoroethyl)-2-(2,2,2-trifluoroethylamino)-2H-pyrrol-5-one was obtained using the procedure above. Compound II-8 was obtained by stirring 4-methyl-1-(2,2,2-trifluoroethyl)-2-(2,2,2-trifluoroethylamino)-2H-pyrrol-5-one in dioxane with conc. HCl (quantitative yield); $^1$H NMR (400 MHz, CDCl$_3$) δ: 6.69 (1H, s), 5.48 (2H, d), 4.25 (1H, m), 3.82 (1H, m), 2.50 (1H, d), 1.94 (3H, s)

Step 2: (1-methoxy-4-methyl-5-oxo-2H-pyrrol-2-yl) N-benzylcarbamate (Ia-3)

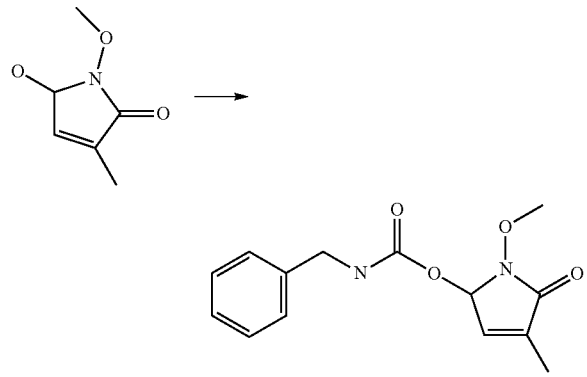

To a solution of 1,2a,7,7a-tetrahydro-2H-cyclobut[a]thioinden-2-one (0.71958 mmol, 0.103 g) in diisopropylether (7 mL) was added triethylamine (0.100 mL, 0.719 mmol) and then benzylisocyanate (0.719 mmol, 0.089 mL). The reaction was stirred overnight at room temperature. The reaction was quenched with saturated ammonium chloride and extracted with ethyl acetate. The combined organic layers were washed with brine, dried and concentrated. The residue was purified by flash chromatography (0% to 100% ethyl acetate in cyclohexane) to give (1-methoxy-4-methyl-5-oxo-2H-pyrrol-2-yl) N-benzylcarbamate Ia-3 (54%, 107 mg). $^1$H NMR (400 MHz, CDCl$_3$) δ: 7.37-7.26 (5H, m), 6.46 (2H, s), 5.26 (1H, brs), 4.43 (2H, d), 3.75 (3H, s), 2.04 (3H, s).

A similar procedure was used to prepare compounds:

(4-methyl-5-oxo-1-prop-2-ynyl-2H-pyrrol-2-yl) N-benzylcarbamate Ia-4; $^1$H NMR (400 MHz, CDCl$_3$) δ: 7.38-7.27 (5H, m), 6.64 (1H, s), 6.52 (1H, s), 5.17 (1H, brs), 4.44-4.39 (3H, m), 4.01 (1H, d), 2.16 (1H, s), 1.96 (3H, s).

[4-methyl-5-oxo-1-(2,2,2-trifluoroethyl)-2H-pyrrol-2-yl] N-benzylcarbamate Ia-5; $^1$H NMR (400 MHz, CDCl$_3$) δ: 7.38-7.27 (5H, m), 6.68 (1H, s), 6.52 (1H, s), 5.17 (1H, brs), 4.42 (2H, m), 4.13 (1H, m), 3.91 (1H, m), 1.95 (3H, s).

(1-cyclopropyl-4-methyl-5-oxo-2H-pyrrol-2-yl) N-benzylcarbamate; $^1$H NMR (400 MHz, CDCl$_3$) δ: 7.38-7.27 (5H, m), 6.54 (1H, s), 6.36 (1H, s), 5.21 (1H, brs), 4.43 (2H, m), 2.50 (1H, m), 1.90 (3H, s), 0.82-0.74 (4H, m).

(4-methyl-5-oxo-1-prop-2-ynyl-2H-pyrrol-2-yl) N-phenylcarbamate Ia-10; $^1$H NMR (400 MHz CDCl$_3$) δ: 1.95 (s, 3H), 2.21 (s, 1H), 4.04 (dd, 1H), 4.44 (d, 1H), 6.59 (s, 1H), 6.69 (s, 1H), 7.00-7.18 (m, 2H) 7.30-7.51 (m, 4H)

(4-methyl-5-oxo-1-prop-2-ynyl-2H-pyrrol-2-yl) N-(3-pyridyl)carbamate Ia-11; $^1$H NMR (400 MHz CDCl$_3$) δ: 1.96 (s, 3H), 2.22 (s, 1H), 4.04 (d, 1H), 4.44 (d, 1H), 6.59 (s, 1H), 6.71 (s, 1H), 7.28-7.44 (m, 2H), 7.93-8.14 (m, 1H), 8.37 (d, 1H), 8.58 (s, 1H).

(1-cyclopropyl-4-methyl-5-oxo-2H-pyrrol-2-yl) N-(4-fluorophenyl)carbamate Ia-12; $^1$H NMR (400 MHz, CDCl$_3$) δ: 0.66-0.96 (m, 4H), 1.90 (s, 3H), 2.38-2.66 (m, 1H), 6.40 (s, 1H), 6.58 (t, 1H), 6.94-7.09 (m, 2H), 7.16 (br. s., 1H), 7.42 (br. M, 2H).

Example 3

Step 1: 2-chloro-4-methyl-1-prop-2-ynyl-2H-pyrrol-5-one

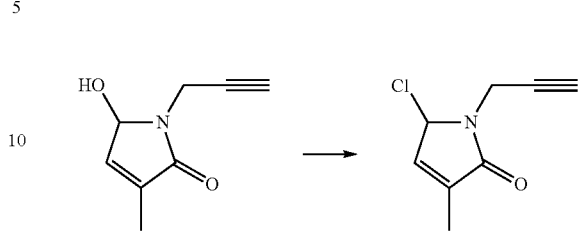

To a solution of 2-hydroxy-4-methyl-1-prop-2-ynyl-2H-pyrrol-5-one II-6 (0.250 g, 1.65 mmol) in dichloromethane (8 mL) under argon was added 1-chloro-N,N,2-trimethyl-1-propenylamine (0.296 mL, 2.15 mmol). The reaction mixture was stirred at room temperature for 2 h and was concentrated in vacuo to give an oil containing the desired product in mixture with N,N,2-trimethylpropanamide. 2-chloro-4-methyl-1-prop-2-ynyl-2H-pyrrol-5-one was used as such for the next step; 1H NMR (400 MHz, CDCl$_3$) 1.96 (t, J=1.47 Hz, 3H), 2.26 (t, 1H), 3.88 (dd, 1H), 4.68 (dd, 1H), 6.04 (s, 1H), 6.77 (s, 1H)

A similar procedure was used to prepare compounds:
2-chloro-4-methyl-1-cyclopropyl-2H-pyrrol-5-one; $^1$H NMR (400 MHz, CDCl$_3$) 0.56-1.07 (m, 4H), 1.90 (s, 3H), 2.54-2.71 (m, 1H), 5.77 (s, 1H), 6.65 (s, 1H)

Step 2: 2-(4-bromophenoxy)-4-methyl-1-prop-2-ynyl-2H-pyrrol-5-one (Ib-1)

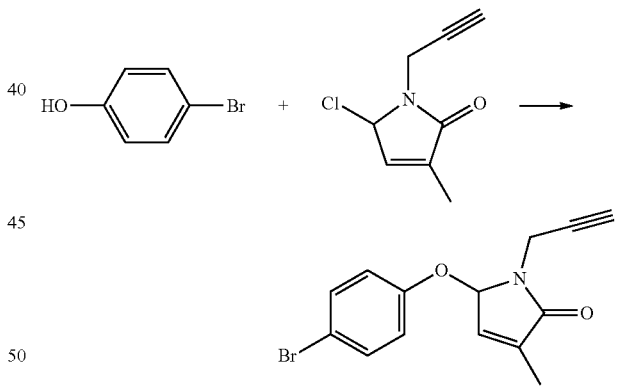

To a solution of 4-bromophenol (0.288 g, 1.65 mmol) in tetrahydrofuran (8 mL) under argon and cooled to 0° C. was added sodium hydride (55-65% in mineral oil, 0.072 g, 1.81 mmol) and the reaction mixture stirred at 0° C. for 30 min. Then, a solution of 2-chloro-4-methyl-1-prop-2-ynyl-2H-pyrrol-5-one III-6 in dichloromethane (8 mL) was added and the reaction mixture was stirred at room temperature overnight. A solution of Na$_2$CO$_3$ (2M) and ethyl acetate were added and the aqueous layer was extracted. The combined organic layers were washed with brine, dried over Na$_2$SO$_4$ and concentrated. The residue was purified by flash chromatography (0% to 100% ethyl acetate in cyclohexane) to give 2-(4-bromophenoxy)-4-methyl-1-prop-2-ynyl-2H-pyrrol-5-one Ib-1 (0.144 g, 28%) as a white solid. M.p.: 92-94°

C.; $^1$H NMR (400 MHz, CDCl$_3$) δ: 1.94 (s, 3H), 2.22 (s, 1H), 3.92 (d, 1H), 4.65 (d, 1H), 5.97 (s, 1H), 6.65-6.71 (m, 1H), 6.92 (d, 2H), 7.42 (d, 2H).

A similar procedure was used to prepare compounds:

2-(4-bromophenoxy)-4-methyl-1-cyclopropyl-2H-pyrrol-5-one Ib-2; 1H NMR (400 MHz, CDCl$_3$) δ: 7.41 (d, 2H), 6.87 (d, 2H), 6.58 (s, 1H), 5.70 (s, 1H), 2.62 (dt, 1H), 1.89 (s, 3H), 0.90-1.05 (m, 1H), 0.64-0.90 (m, 3H).

TABLE 3

Compounds of Formula (Ia)

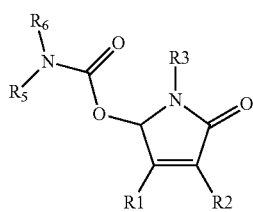

Ia

| Example | R1 | R2 | R3 | R5 | R6 | $^1$H NMR (400 MHz, CDCl$_3$) δ |
|---|---|---|---|---|---|---|
| Ia-1 | H | Me | CH$_2$OMe | H | Bn | 7.32-7.23 (5 H, m), 6.64 (1 H, s), 6.53 (1 H, s), 5.49 (1 H, m), 4.89 (1 H, d), 4.69 (1 H, d), 4.39 (2 H, m), 3.26 (3 H, s), 1.91 (3 H, s) |
| Ia-2 | H | Me | Me | H | Bn | 7.35-7.25 (5 H, m), 6.51 (1 H, s), 6.26 (1H, s), 5.75 (1 H, brs), 4.39 (2 H, d), 2.88 (3 H, s), 1.88 (3 H, s). |
| Ia-3 | H | Me | OMe | H | Bn | 7.37-7.26 (5 H, m), 6.46 (2 H, s), 5.26 (1 H, brs), 4.43 (2 H, d), 3.75 (3 H, s), 2.04 (3 H, s) |
| Ia-4 | H | Me | CH$_2$CCH | H | Bn | 7.38-7.27 (5 H, m), 6.64 (1 H, s), 6.52 (1 H, s), 5.17 (1 H, brs), 4.44-4.39 (3 H, m), 4.01 (1 H, d), 2.16 (1 H, s), 1.96 (3 H, s). |
| Ia-5 | H | Me | CH$_2$CF$_3$ | H | Bn | 7.38-7.27 (5 H, m), 6.68 (1 H, s), 6.52 (1 H, s), 5.17 (1 H, brs), 4.42 (2 H, m), 4.13 (1 H, m), 3.91 (1 H, m), 1.95 (3 H, s). |
| Ia-6 | H | Me | CH(CH$_2$CH$_2$) | H | Bn | 7.38-7.27 (5 H, m), 6.54 (1 H, s), 6.36 (1 H, s), 5.21 (1 H, brs), 4.43 (2 H, m), 2.50 (1 H, m), 1.90 (3 H, s), 0.82-0.74 (4 H, m) |
| Ia-7 | H | Me | Ph | H | Bn | 7.54 (d, 2H), 7.15-7.39 (m, 8H), 7.00 (s, 1H), 6.71-6.74 (m, 1H), 5.19 (s, 1H), 4.34 (dd, 2H), 1.96 (s, 3H). |
| Ia-8 | H | Me | 3-pyridyl | H | Bn | 1.90 (m, 3 H), 4.16 (m, 2 H), 7.06-7.18 (m, 4 H), 7.19-7.34 (m, 3 H), 7.45 (dd, 1 H), 7.89-7.97 (m, 1 H), 8.04 (t, 1 H), 8.42 (dd, 1 H), 8.77 (d, 1 H). |
| Ia-9 | H | Me | 2-thiazoyl | H | Bn | 2.08-2.23 (s, 3 H), 4.39 (dd, 1 H), 4.54-4.68 (dd, 1 H), 5.21 (m, 1 H), 6.09 (m, 1 H), 6.92-7.03 (d, 1 H), 7.28-7.39 (m, 6 H), 7.42 (d, 1 H). |
| Ia-10 | H | Me | CH$_2$CCH | H | Ph | 1.95 (s, 3 H), 2.21 (s, 1 H), 4.04 (dd, 1 H), 4.44 (d, 1 H), 6.59 (s, 1 H), 6.69 (s, 1 H), 7.00-7.18 (m, 2 H) 7.30-7.51 (m, 4 H) |

TABLE 3-continued

Compounds of Formula (Ia)

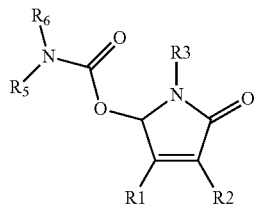

Ia

| Example | R1 | R2 | R3 | R5 | R6 | $^1$H NMR (400 MHz, CDCl$_3$) δ |
|---|---|---|---|---|---|---|
| Ia-11 | H | Me | CH$_2$CCH | H | 2-Py | 1.96 (s, 3 H), 2.22 (s, 1 H), 4.04 (d, 1 H), 4.44 (d, 1 H), 6.59 (s, 1 H), 6.71 (s, 1 H), 7.28-7.44 (m, 2 H), 7.93-8.14 (m, 1 H), 8.37 (d, 1 H), 8.58 (s, 1 H) |
| Ia-12 | H | Me | CH(CH$_2$CH$_2$) | H | 4-F—Ph | 0.66-0.96 (m, 4 H), 1.90 (s, 3 H), 2.38-2.66 (m, 1 H), 6.40 (s, 1 H), 6.58 (t, 1 H), 6.94-7.09 (m, 2 H), 7.16 (br. s., 1 H), 7.42 (br. m, 2 H) |

TABLE 4

Compounds of Formula (Ib)

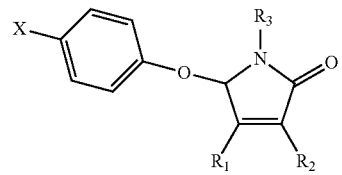

Ib

| Example | R1 | R2 | R3 | X | $^1$H NMR (400 MHz, CDCl$_3$) δ |
|---|---|---|---|---|---|
| Ib-1 | H | Me | CH$_2$CCH | Br | 7.32-7.23 (5 H, m), 6.64 (1 H, s), 6.53 (1 H, s), 5.49 (1 H, m), 4.89 (1 H, d), 4.69 (1 H, d), 4.39 (2 H, m), 3.26 (3 H, s), 1.91 (3 H, s) |
| Ib-2 | H | Me | CH(CH$_2$CH$_2$) | Br | 7.35-7.25 (5 H, m), 6.51 (1 H, s), 6.26 (1H, s), 5.75 (1 H, brs), 4.39 (2 H, d), 2.88 (3 H, s), 1.88 (3 H, s). |

TABLE 5

Compounds of Formula (II)

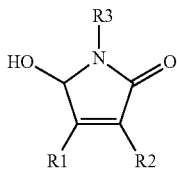

II

| Example | R1 | R2 | R3 | $^1$H NMR (400 MHz, CDCl$_3$) δ |
|---|---|---|---|---|
| II-1 | H | Me | CH$_2$OMe | 6.65 (1 H, s), 5.50 (1 H, d), 4.90 (1 H, d), 4.73 (1 H, d), 3.97 (1 H, d), 3.33 (3H, s), 1.90 (3 H, s) |

TABLE 5-continued

Compounds of Formula (II)

$$\text{Structure II: 5-membered ring with HO-CH at position, N-R3, C=O, and R1, R2 substituents}$$

| Example | R1 | R2 | R3 | $^1$H NMR (400 MHz, CDCl$_3$) δ |
|---------|----|----|----|-----|
| II-2 | H | Me | Me | 6.54 (1 H, s), 5.16 (1 H, d), 3.86 (1 H, d), 2.91 (3H, s), 1.83 (3H, s) |
| II-3 | H | Me | OMe | 6.47 (1 H, s), 5.47 (1 H, s), 3.93 (3 H, s), 1.91 (3 H, s). |
| II-4 | H | Me | Bn | 7.34-7.20 (5 H, m), 6.54 (1 H, s), 5.16 (1 H, d), 4.94 (1 H, d), 4.30 (1 H, d), 2.38 (1 H, d), 1.91 (3 H, s) |
| II-5 | H | Me | CH(CH$_2$CH$_2$) | 6.49 (1 H, s), 5.22 (1 H, brs), 3.61 (1H, brs), 2.61 (1 H, m), 1.83 (3 H, s), 1.01-0.66 (4 H, m). |
| II-6 | H | Me | CH$_2$CCH | 6.65 (1 H, s), 5.52 (1 H, d), 4.53 (1 H, d), 4.02 (1 H, d), 2.27 (1 H, s), 2.20 (1 H, d), 1.94 (3 H, s). |
| II-7 | H | Me | CHMe$_2$ | 6.50 (1 H, s), 5.41 (1 H, d), 4.24 (1 H, m), 2.06 (1 H, d), 1.88 (3 H, s), 1.34 (6 H, m) |
| II-8 | H | Me | CH$_2$CF$_3$ | 6.69 (1 H, s), 5.48 (2 H, d), 4.25 (1 H, m), 3.82 (1 H, m), 2.50 (1 H, d), 1.94 (3 H, s) |
| II-9 | H | Me | Ph | 1.90 (s, 3 H), 2.72 (d, 1 H), 5.85 (d, 1 H), 6.68 (t, 1 H), 7.18 (d, 1 H), 7.39 (t, 2 H), 7.71 (d, 2 H) |
| II-10 | H | Me | 3-pyridyl | 1.86 (t, 3 H), 6.00 (d, 1 H), 6.52 (d, 1 H), 6.93 (s, 1 H), 7.36-7.47 (m, 1 H), 8.08 (dd, 1 H), 8.33 (dd, 1 H) 8.90 (s, 1 H) |
| II-11 | H | Me | 2-thiazoyl | 2.15-2.25 (s, 3 H), 5.25 (s, 1 H), 6.02 (s, 1 H), 6.06 (s, 1 H), 6.98 (d, 1 H), 7.42 (d, 1 H) |

Biological Examples

The effect of compounds of Formula (I) on germination of *Orobanche cumana* Wallr. seeds was evaluated on glass fiber filter paper (GFFP) in petri dishes. Seeds were preconditioned at moisture and suitable temperature to become responsive to the specific chemical germination stimulants.

Test compounds were dissolved in DMSO (10,000 mg/L) and stored at room temperature in a desiccators with desiccants. The stock solutions were dissolved with deionised water to the appropriate final test concentration.

Seeds of *O. cumana* race 'F' were collected from sunflower fields in Manzanilla (Seville, Spain) in 2008 (seed lot IN153) and stored at room temperature. To separate seeds from heavy organic debris, a modified sucrose floatation technique as described by Hartman & Tanimonure (Plant Disease (1991), 75, p. 494) was applied. Seeds were filled into a separation funnel and stirred in water. When seeds floated to the surface, the water fraction containing heavy debris was discarded. Seeds were re-suspended in 2.5 M sucrose solution (specific gravity of 1.20) and heavy debris was allowed to settle down for 60 min. After removing debris, seeds were disinfected in 1% sodium hypochlorite solution and 0.025% (v/v) Tween 20 for 2 min. The seeds were decanted onto two layers of cheesecloth, rinsed with sterile deionised water and re-suspended in sterile deionised water. 2 mL of the seed suspension containing approximately 150-400 seeds was spread evenly on two layers of sterile glass fiber filter paper disc (Ø9 mm) in Petri dishes (Ø9 cm). After wetting the discs with 3 mL sterile deionised water, petri dishes were sealed with parafilm. Seeds were incubated for 10 days at 20° C. in the dark for seed conditioning. The upper disc with conditioned seeds was briefly dried, transferred to a petri dish lined with a dry GFFP disc, and wetted with 6 mL of the appropriate test solution. The compounds of Formula (I) were tested at concentrations of 0.01, 0.1, and 1 mg/L. The strigolactone analogue GR24 (commercially available as a mixture of isomers) was included as positive control and 0.01% DMSO as negative control. All treatments were tested in five replicates. Seeds were re-incubated at 20° C. in the dark and examined for germination 10 days later. The radicles of germinated seeds were stained for 5 min with blue ink (PELIKAN #4001, Germany) in 5% acetic acid according to Long et al. (Seed Science Research (2008), 18, p. 125). After staining, seeds were photographed using a camera stand mounted with a digital SLR camera (Canon EOS 5D). Germination of 100 seeds per replicate was evaluated on digital images. Seeds were considered germinated when the radicle protruded from the seed coat. The results of the *Orobanche* seed germination tests are shown in Tables 5 and Table 6.

TABLE 5

Effect of strigolactone analogs on germination of preconditioned *Orobanche cumana* seeds at 1 mg/L

| Compound | Germination (%)* |
|----------|------------------|
| Ia-1 | 86.8 |
| Ia-2 | 76.6 |
| Ia-3 | 44.8 |
| Ia-5 | 16.2 |
| Ia-6 | 76.4 |

*N = 5 × 100 seeds; control (0.01% DMSO): 0.75% germination

TABLE 6

Comparison of strigolactone analogs on the germination of preconditioned *Orobanche cumana* seeds.

| Compound | Concentration (mg/L) | | |
|----------|---|---|---|
| | 1 | 0.1 | 0.01 |
| | -Germination (%)*- | | |
| [structure with benzyl carbamate linked to N-methyl pyrrolinone] | 76.6 | 67.4 | 60.8 |
| Ia-2 (from WO11125714) [structure with benzyl carbamate linked to furanone] | 82.6 | 41.8 | 8.8 |

TABLE 6-continued

Comparison of strigolactone analogs on the germination of preconditioned *Orobanche cumana* seeds.

| Compound | Concentration (mg/L) | | |
|---|---|---|---|
| | 1 | 0.1 | 0.01 |
| GR-24 | 86.6 | 78.4 | 65 |

*N = 5 × 100 seeds; control (0.01% DMSO): 1.4% germination

The invention claimed is:

1. A compound of Formula (I)

(I)

wherein:

W is selected from O, S, SO or $SO_2$;

R1 and R2 are independently selected from H, C1-C6 alkyl, C1-C6 haloalkyl, halogen, C1-C6 alkoxy, aryloxy, C1-C6 alkylsulfinyl, C1-C6 alkylsulfonyl, C1-C6 alkylthio; or R1 and R2 form a C5 or C6 cycloalkyl;

R3 is selected from H, C1-C6 alkyl optionally substituted by one to five R4, hydroxyl, C1-C6 alkoxy, cyano, nitro, C1-C6 sulfonylalkyl, acetyl, C1-C6 alkoxycarbonyl, C3-C6 cycloalkyl optionally substituted by R4, C2-C6 alkenyl optionally substituted by one to five R4, C2-C6 alkynyl optionally substituted by one to five R4, C3-C6 heterocyclyl optionally substituted by one to five R4; or R3 is selected from benzyl or aryl, each optionally substituted with C1-C3 alkyl, C1-C3 alkoxy, C1-C3 alkylalkoxy, cyano, nitro, halogen or with C1-C3 haloalkyl; wherein R4 is selected from halogen, C1-C3 alkyl, C1-C3 haloalkyl, C1-C3 alkoxy, cyano or nitro;

Q is selected from one of (i) or (ii):

(i)

wherein X is selected from H, C1-C3 alkyl, halogen, C1-C3 alkoxy, C1-C3 alkoxyalkyl, C1-C3 haloalkyl, C1-C3 cyanoalkyl, cyano, nitro, C1-C3 sulfonylalkyl, C2-C3 alkynyl, acetoxy, C1-C3 alkylcarbonyl, C1-C3 alkoxycarbonyl, carboxyl, phenyl or phenyl substituted with C1-C3 alkyl, C1-C3 alkoxy, C1-C3 haloalkyl, C1-C3 alkylcyano or with cyano;

R8 is selected from C1-C3 alkyl, C1-C3 alkoxy, halogen, C1-C3 haloalkyl, cyano, and nitro; and n is selected from 0 to 4;

ii)

(ii)

wherein Y is selected from O or S;

R5 is selected from hydrogen or C1-C6 alkyl;

R6 is selected from C1-C6 alkyl optionally substituted with halogen, C1-C3 alkoxy, cyano, nitro; or R6 is aryl or heteroaryl each optionally substituted with R9; wherein R9 is selected from halogen, C1-C3 haloalkyl, C1-C3 alkyl, C1-C3 alkoxy, cyano, or nitro;

or salts or N-oxides thereof;

with the provisos that:

a) when R1 and R2 form a C6 cycloalkyl, then R3 cannot be substituted phenyl; or b) when R1 and R2 form a C6 cycloalkyl and Q is (ii), then R3 cannot be heteroaryl substituted or unsubstituted; or c) when R1 and R2 are both methyl, W is O and Q is (ii), then R3 cannot be substituted heteroaryl or substituted phenyl or unsubstituted heteroaryl; or d) when R1 and R2 are both methyl, W is O and Q is an unsubstituted phenyl, then R3 cannot be benzyl; or e) when R1 and R2 are both methyl, W is S and Q is (i), then R3 cannot be benzyl, butyl, substituted heteroaryl or substituted phenyl; or f) when R1 and R2 are both chlorine, W is S and Q is an unsubstituted phenyl, then R3 cannot be 2,4-dimethoxybenzyl; or g) when R1 and R2 are both hydrogen, W is S and Q is an unsubstituted phenyl, then R3 cannot be tertbutoxycarbonyl; or h) when W is $SO_2$ and Q is (i), then R3 cannot be H or tertbutoxycarbonyl.

2. The compound according to claim 1 wherein R1 and R2 are independently selected from H, methyl, ethyl, halogen or methoxy or form a C6 cycloalkyl.

3. The compound according to claim 1 wherein R1 and R2 are independently selected from H and methyl.

4. The compound according to claim 1 wherein R1 and R2 are both methyl.

5. The compound according to claim 1 wherein one of R1 and R2 is hydrogen and the other is methyl.

6. The compound according to claim 1 wherein R3 is selected from H, C1-C6 alkyl optionally substituted by one to five R4, methoxy, ethoxy, cyano, acetyl, acetoxy, cyclopropyl optionally substituted with R4, C1-C6 alkenyl optionally substituted by one to five R4, and C1-C6 alkynyl optionally substituted by one to five R4.

7. The compound according to claim 1 wherein R3 is selected from hydrogen, methyl, ethyl, butyl, isopropyl, trifluoromethyl, trifluoroethyl, methoxymethyl, methoxyethyl, methoxy, ethoxy, cyano, acetyl, acetoxy, cyclopropyl, allyl, propargyl, phenyl, benzyl, pyridyl or thiazolyl.

8. The compound according to claim 1 wherein X is selected from H, methyl, ethyl, iso-propyl, halogen, alkoxy, alkoxyalkyl, haloalkyl, cyano, nitro, acetylene, acetoxy, acetyl, carboxyl, methoxycarbonyl, or from unsubstituted phenyl.

9. The compound according to claim 1 wherein X is selected from H, methyl, ethyl, chlorine, fluorine, bromine, trifluoromethyl, methoxymethyl, methoxyethyl, methoxy, ethoxy, cyano, nitro, acetylene, acetoxy or from unsubstituted phenyl.

10. The compound according to claim 1 wherein R8 is methyl, ethyl, methoxy, ethoxy, chlorine, fluorine, bromine, haloalkyl, cyano, and nitro and n is selected from 0 to 4.

11. The compound according to claim 1 wherein R8 is methyl, methoxy, chlorine, fluorine, bromine, trifluoromethyl, cyano, nitro and n is selected from 0 to 2.

12. A plant growth regulator or seed germination promoting composition, comprising a compound according to claim 1 and an agriculturally acceptable formulation adjuvant.

13. A method for regulating the growth of plants at a locus, wherein the method comprises applying to the locus a plant growth regulating amount of a composition according to claim 12.

14. A method for promoting the germination of seeds comprising applying to the seeds, or a locus containing seeds, a seed germination promoting amount of a composition according to claim 12.

15. A method for controlling weeds comprising applying to a locus containing weed seeds a seed germination promoting amount of a composition according to claim 12 allowing the seeds to germinate, and then applying to the locus a post-emergence herbicide.

* * * * *